(12) United States Patent
Krom et al.

(10) Patent No.: US 12,702,440 B2
(45) Date of Patent: Aug. 11, 2026

(54) ANCHORED GUIDE TUBES FOR INSERTION AND STABILIZATION OF DEVICES IN BODY WALL, SYSTEMS, AND METHODS

(71) Applicant: INTUITIVE SURGICAL OPERATIONS, INC., Sunnyvale, CA (US)

(72) Inventors: Justin Krom, Southington, CT (US); Ronald G. Litke, Sandy Hook, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 774 days.

(21) Appl. No.: 17/356,713

(22) Filed: Jun. 24, 2021

(65) Prior Publication Data

US 2021/0315609 A1 Oct. 14, 2021

Related U.S. Application Data

(63) Continuation-in-part of application No. PCT/US2019/068228, filed on Dec. 23, 2019, and a (Continued)

(51) Int. Cl.
*A61B 17/34* (2006.01)
*A61B 17/00* (2006.01)

(52) U.S. Cl.
CPC .................... *A61B 17/3423* (2013.01); *A61B 2017/00407* (2013.01); *A61B 2017/3486* (2013.01); *A61B 2017/349* (2013.01); *A61B 2017/3492* (2013.01)

(58) Field of Classification Search
CPC .......... A61B 17/3423; A61B 2017/349; A61B 2017/3486; A61B 2017/3492
See application file for complete search history.

(56) References Cited

U.S. PATENT DOCUMENTS 5,002,557 A 3/1991 Hasson
5,147,316 A 9/1992 Castillenti
(Continued)

FOREIGN PATENT DOCUMENTS

CN 105852911 A 8/2016
CN 107095707 A * 8/2017 ......... A61B 17/3478
(Continued)

OTHER PUBLICATIONS

CN 107095707 A Espacenet translation (Year: 2017).*
(Continued)

*Primary Examiner* — Katherine H Schwiker
*Assistant Examiner* — Zehra Jaffri
(74) *Attorney, Agent, or Firm* — Jones Burke, PLLC

(57) ABSTRACT

A medical device includes a tube comprising a proximal end, a distal end, a wall extending from the proximal end to the distal end of the tube and surrounding a hollow interior of the tube, and one or more engagement features on the lateral wall. An inflatable member is located at a distal end portion of the tube. The medical device also includes a repositionable anchor located on the tube proximal to the inflatable anchor and configured to engage the one or more features on the lateral wall. In a first configuration of the medical device, the repositionable anchor is translatable along the tube, and in a second configuration of the medical device the repositionable anchor is fixed in translation relative to the tube.

20 Claims, 19 Drawing Sheets

Related U.S. Application Data continuation-in-part of application No. PCT/US2019/068229, filed on Dec. 23, 2019, and a continuation-in-part of application No. PCT/US2019/068227, filed on Dec. 23, 2019, and a continuation-in-part of application No. PCT/US2019/068226, filed on Dec. 23, 2019.

(60) Provisional application No. 62/785,030, filed on Dec. 26, 2018, provisional application No. 62/785,033, filed on Dec. 26, 2018, provisional application No. 62/785,035, filed on Dec. 26, 2018, provisional application No. 62/785,027, filed on Dec. 26, 2018.

(56) References Cited

U.S. PATENT DOCUMENTS 5,556,411 A 9/1996 Taoda et al.
5,707,357 A 1/1998 Mikhail et al.
5,713,869 A 2/1998 Morejon
5,957,888 A 9/1999 Hinchliffe
5,964,781 A 10/1999 Mollenauer et al.
6,796,960 B2* 9/2004 Cioanta .................. A61B 18/04 604/103.01
6,908,454 B2 6/2005 McFarlane
8,066,673 B2 11/2011 Hart et al.
8,147,453 B2 4/2012 Albrecht et al.
8,852,208 B2 10/2014 Gomez et al.
8,888,692 B1 11/2014 Pravongviengkham et al.
9,149,272 B2 10/2015 Sherts et al.
9,295,524 B2 3/2016 Schena et al.
9,358,074 B2 6/2016 Schena et al.
2002/0042606 A1* 4/2002 Castaneda .......... A61B 17/3417 606/1
2003/0040753 A1 2/2003 Daum et al.
2004/0111061 A1 6/2004 Curran
2004/0116894 A1 6/2004 DeLegge
2005/0165432 A1 7/2005 Heinrich
2006/0142779 A1* 6/2006 Arramon ............ A61B 17/3421 606/92
2007/0239108 A1 10/2007 Albrecht et al.
2009/0204081 A1* 8/2009 Whittaker .......... A61B 17/3421 604/264
2010/0010449 A1 1/2010 Leibowitz et al.
2015/0073223 A1* 3/2015 Pravongviengkham .................... A61B 17/0218 600/207
2015/0150595 A1 6/2015 Pattison et al.
2016/0220271 A1 8/2016 Mastri
2018/0168684 A1 6/2018 Burbank et al.
2018/0271557 A1* 9/2018 Buyda ................ A61B 17/3423
2019/0038313 A1 2/2019 Hendershot, III

FOREIGN PATENT DOCUMENTS

JP 2015061550 A 4/2015
WO WO-9415657 A1 7/1994
WO WO-0108563 A2 2/2001
WO WO-02066108 A1 8/2002
WO WO-2016196276 A1 12/2016

OTHER PUBLICATIONS

International Search Report and Written Opinion for Application No. PCT/US2019/068226, mailed Apr. 29, 2020, 13 pages.
International Search Report and Written Opinion for Application No. PCT/US2019/068227, mailed Apr. 29, 2020, 12 pages.
International Search Report and Written Opinion for Application No. PCT/US2019/068228, mailed Apr. 29, 2020, 11 pages.
International Search Report and Written Opinion for Application No. PCT/US2019/068229, mailed Apr. 24, 2020, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner 438
458
454
456
455
$W_1$
464
$D_2$
460
$W_2$
T
462
$D_1$
$T_r$
452
464

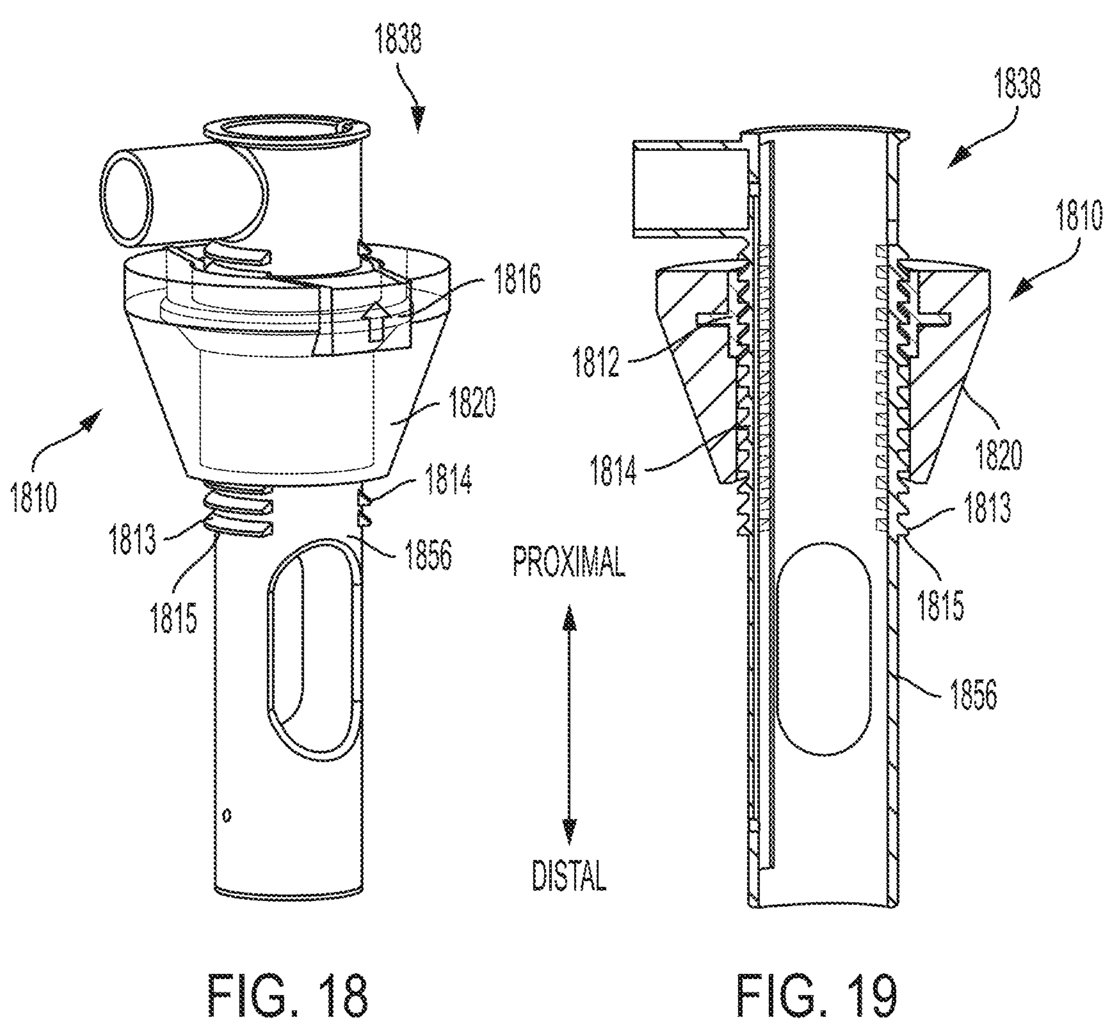
FIG. 18
FIG. 19
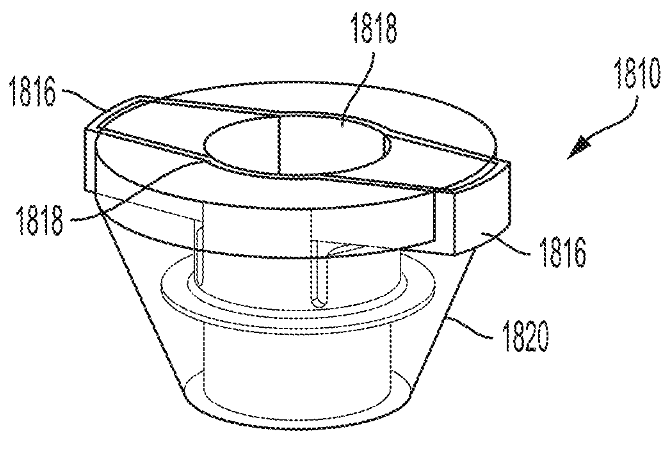
FIG. 20

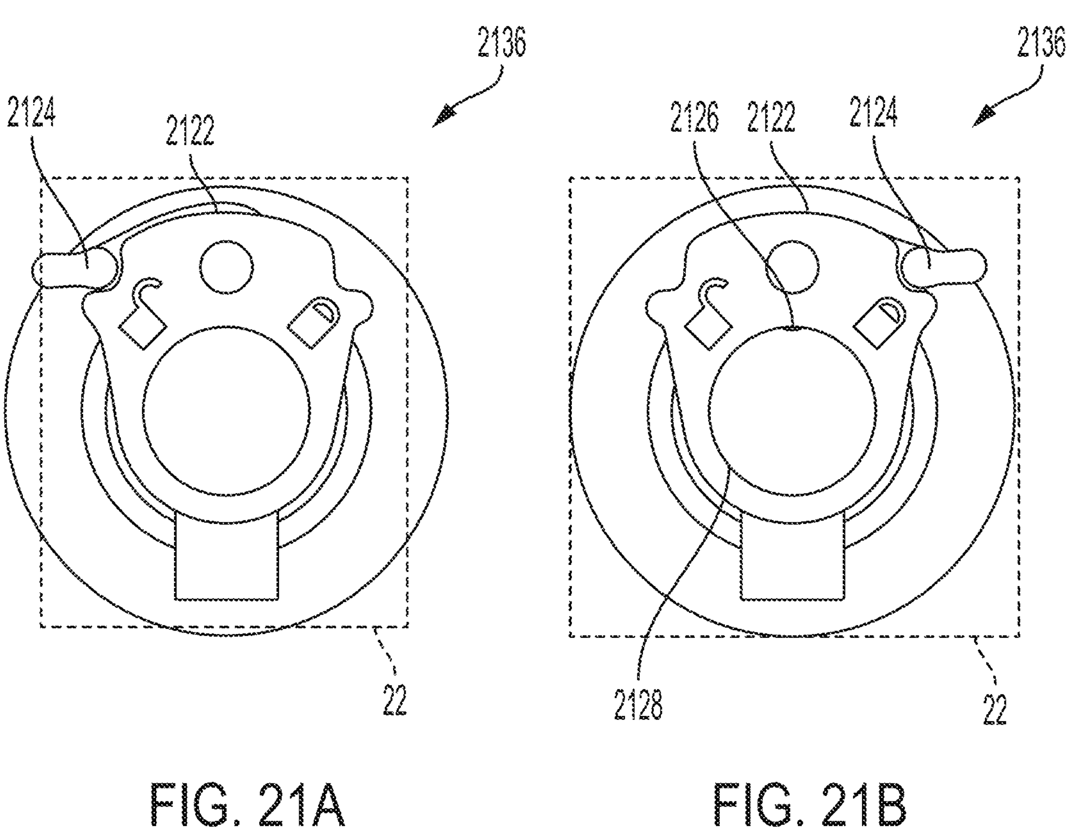
FIG. 21A
FIG. 21B
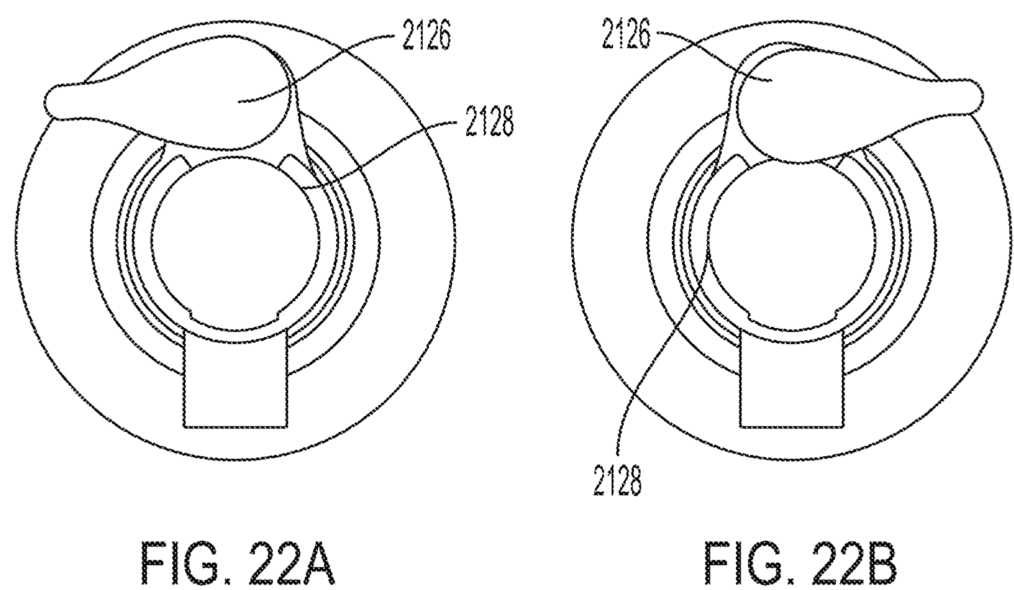
FIG. 22A
FIG. 22B

ANCHORED GUIDE TUBES FOR INSERTION AND STABILIZATION OF DEVICES IN BODY WALL, SYSTEMS, AND METHODS

CROSS-REFERENCE TO RELATED APPLICATIONS

This application is a continuation-in-part of each of International Patent Application Nos. PCT/US2019/068226, PCT/US2019/068227, PCT/US2019/068228, and PCT/US2019/068229 (each filed Dec. 23, 2019). International Patent Application No. PCT/US2019/068226 claims priority to U.S. Provisional Application No. 62/785,027, filed Dec. 26, 2018. International Patent Application No. PCT/US2019/068227 claims priority to U.S. Provisional Application No. 62/785,030, filed Dec. 26, 2018. International Patent Application No. PCT/US2019/068228 claims priority to U.S. Provisional Application No. 62/785,033, filed Dec. 26, 2018. International Patent Application No. PCT/US2019/068229 claims priority to U.S. Provisional Application No. 62/785,035, filed Dec. 26, 2018. The entire content of each of the above-identified applications is incorporated by reference herein in their entireties.

TECHNICAL FIELD

Aspects of the present disclosure relate to anchored guide devices, systems, and methods for receiving, positioning, and stabilizing a position of a cannula in a body wall to provide access to a remote site within the body. For example, the present disclosure relates to an anchored guide device that is a component of a balloon trocar assembly.

INTRODUCTION

Various surgical instruments or tools can be positioned to extend through cannulas passing through an incision or other opening in a patient's body wall. Such surgical instruments may be configured to seal, bond, ablate, fulgurate, sense, irrigate, suction, measure, or perform other treatments or procedures and/or diagnostic procedures at a remote site on the patient's body (broadly referred to as "surgical procedures" or "remote procedures" herein). Thus, a "surgical instrument," as used in the present disclosure, is broadly construed and can include instruments with end effectors, endoscopes, and various other types of instruments positioned to extend through a cannula or directly inserted through an incision in the patient's body wall. Such surgical instruments include, without limitation, minimally invasive surgical instruments that are manually operated or teleoperated using computer-assisted technology. One example of a teleoperated, computer-assisted surgical system (e.g., a robotic system that provides telepresence) with which embodiments of the present disclosure may be used, are the da Vinci® Surgical Systems manufactured by Intuitive Surgical, Inc. of Sunnyvale, Calif.

In some arrangements, a cannula is provided with a seal at a proximal end (end intended to be further from the remote site and outside of the body) and an obturator coupled to the seal that extends through the cannula and out of a distal end (end intended to be closer to the remote site), often referred to as a "trocar." Various devices are used to position and stabilize the cannula relative to the body wall through which it is inserted, either directly or through one or more port or trocar structures, during a remote procedure. A need exists to provide devices, systems, and methods that position, retain, and/or stabilize cannulas within a body wall for use during a procedure at a remote site within the body. In particular, it is desired to provide anchored guide devices, systems, and methods that can be used to position and stabilize a variety of cannula designs, including existing cannula designs.

SUMMARY

Embodiments of the present disclosure may demonstrate one or more of the above-mentioned desirable features. Other features and/or advantages may become apparent from the description that follows.

In one aspect of the present disclosure, a medical device includes a tube having a proximal end, a distal end, a wall extending from the proximal end to the distal end of the tube and surrounding a hollow interior of the tube, and an engagement feature on the lateral wall of the tube. An inflatable member is located at a distal end portion of the tube. The medical device also includes a repositionable anchor located on the tube proximal to the inflatable anchor and configured to engage the engagement feature on the lateral wall of the tube. In a first configuration of the medical device the repositionable anchor is translatable along the tube, and in a second configuration of the medical device the repositionable anchor is fixed in translation relative to the tube.

In another aspect of the disclosure, a medical device includes a tube comprising a proximal end, a distal end, and a wall extending from the proximal end to the distal end of the tube and surrounding a hollow interior of the tube, the tube comprising external threads. An inflatable member is located at a distal end portion of the tube. A repositionable anchor is located on the tube proximal to the inflatable anchor. The repositionable anchor comprises a threaded interior configured to engage with the external threads of the tube. The external threads and internal threads each comprise multiple leads.

In another aspect of the present disclosure, a medical device includes a tube comprising a proximal end, a distal end, and only a single wall extending longitudinally between the proximal and distal ends of the tube, the wall comprising a proximal portion and a distal portion. The device further includes a port in flow communication with an exterior of the tube at the proximal portion of the tube. An inflatable member surrounds the wall at the distal portion of the tube. A fluid passage extends longitudinally through the wall of the tube, the fluid passage comprising a first end and an opposite second end, the first end of the fluid passage being in flow communication with the port, and the second end of the fluid passage being in flow communication with the inflatable member.

In another aspect of the present disclosure, a method of making a medical device includes forming a channel extending longitudinally along an interior surface of a single-wall tube, the channel being in flow communication with an inlet port at a proximal end portion of the tube and an outlet port extending from the channel and opening to an outer surface of the single-wall tube proximate the distal end portion of the single-wall tube. The method further includes enclosing the channel to form an inflation lumen and attaching an inflatable member to the single-wall tube in a position in fluid communication with the outlet port.

In another aspect of the disclosure, a method of using a medical device includes inserting a distal end portion device tube through an incision in a body wall such that the distal end portion is positioned beyond an inner surface of the body wall. The method further includes flowing fluid through an inflation lumen extending at least partially within a thickness of a wall of the tube, inflating an inflatable member located on the distal end portion with the fluid, and moving a repositionable anchor along a length of the tube to a position against an outer surface of the body wall.

In another aspect of the present disclosure, a medical device includes a tube having a proximal end, a distal end, and a lateral wall extending from the proximal end to the distal end of the tube. The lateral wall surrounds a hollow interior of the tube. An inflatable member is located at a distal end portion of the tube. A first opening is defined in the lateral wall of the tube proximal to the inflatable member, and the first opening extending through the lateral wall of the tube from an exterior of the lateral wall to the hollow interior of the tube.

In another aspect of the present disclosure, a method of using a guide device includes inserting a cannula comprising at least one electrically conductive component in a tube of the guide device, inserting the cannula and guide device within an incision in a patient's body wall, and exposing the at least one electrically conductive component of the cannula to the patient's body wall through an opening in a lateral wall of the hollow tube.

In another aspect of the present disclosure, a medical device includes a tube comprising a proximal end, a distal end, and a wall extending from the proximal end to a distal end of the tube and surrounding a hollow interior of the tube. An inflatable member is located at a distal end portion of the tube. An actuatable clamping mechanism is positioned at a first location proximate a proximal end portion of the tube, and the clamping mechanism is actuatable between an open position and a closed position. In the open position, a lateral dimension of the interior of the tube at the first location is larger than in the closed position.

In another aspect of the present disclosure, a system includes a guide device and a cannula. The guide device includes a tube, an inflatable member, and an actuatable clamping mechanism. The tube has a proximal end, a distal end, and a wall extending from the proximal end to the distal end of the tube and surrounding a hollow interior of the tube. The inflatable member is located at a distal end portion of the tube. The actuatable clamping mechanism is positioned at a first location proximate a proximal end portion of the tube. The clamping mechanism is actuatable between an open position and a closed position. In the open position, a lateral dimension of the interior of the tube at the first location is larger in the open position than in the closed position. The system further includes a cannula received within the tube.

In another aspect of the present disclosure, a trocar assembly includes a guide device. The guide device includes a tube comprising a proximal end, a distal end, and a wall extending from the proximal end to the distal end of the tube and surrounding a hollow interior of the tube. A cannula is received within the tube, and an obturator is received within the cannula. An actuatable clamping mechanism is configured to selectively retain the cannula within the tube.

In another aspect of the present disclosure, a method includes inserting a cannula within a tubular member of a guide device and actuating an actuatable clamping mechanism of the guide device from an open position to a closed position to retain the cannula in a fixed position within the tubular member of the guide device.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings:

FIG. 18 is a perspective view of an anchored guide device according to another embodiment of the present disclosure.

FIG. 19 is a longitudinal, cross-sectional view of the anchored guide device of FIG. 18.

FIG. 20 is a perspective view of a repositionable anchor of the anchored guide device of FIG. 18.

FIG. 21A is a top view of a proximal latch device of an anchored guide device in an unlocked position according to the present disclosure.

FIG. 21B is a top view of the proximal latch device of the anchored guide device of FIG. 21A in a locked position.

FIG. 22A is a section view 22-22 of the proximal latch device of FIG. 21A in the unlocked position.

FIG. 22B is a section view 22-22 of the proximal latch device of FIG. 22A in the locked position.

DETAILED DESCRIPTION

Figure 1:
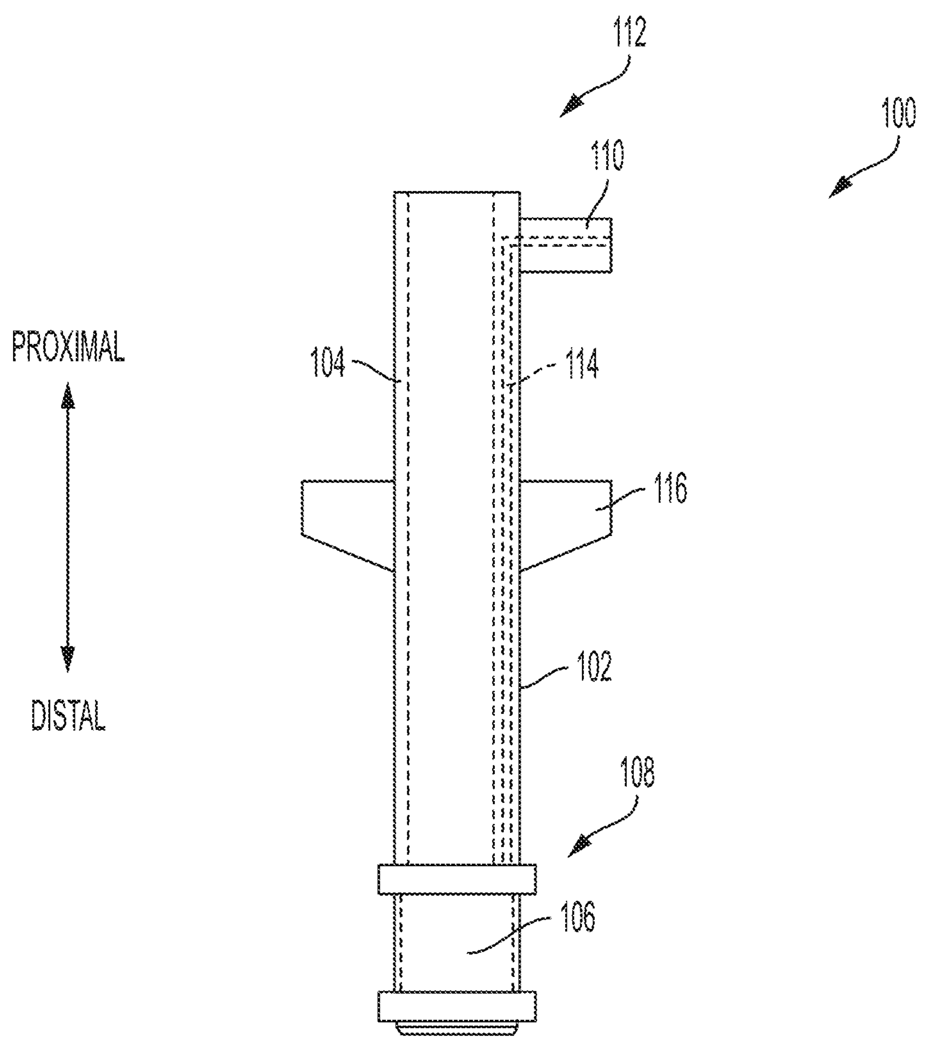
FIG. 1 is a schematic, side view of an anchored guide device according to the present disclosure.

The present disclosure contemplates various medical devices and include anchored guide devices that can be a component of a trocar assembly for receiving, positioning, and stabilizing a cannula relative to a body wall while accessing a remote site in a patient's body.

Various embodiments of the present disclosure contemplate a single-walled tubular guide device component of a trocar assembly that allows for inflation of an inflatable anchor member (balloon) through a port that remains outside the body when the inflatable anchor member is positioned within the body against the body wall. The single-walled tube provides a low overall diameter of the guide device, enabling a correspondingly small-diameter incision in the body wall. Various embodiments use an inflation lumen to provide fluid communication between the port and the inflatable anchor member. The inflation lumen can optionally comprise a recessed channel formed in the single wall of the tube and sealed by a cover member to form a closed lumen. The cover member can have a non-tubular shape. Alternatively, in another embodiment, the inflation lumen can optionally be defined by a separate tube disposed (such as by overmolding) in a recess formed in the single wall of the anchored guide device.

Various embodiments further contemplate an anchored guide device that is made of plastic and provides contact between a cannula inserted within the guide device and a body wall. Such contact can ensure that the cannula, an instrument inserted through the cannula, and the patient's body are at the same voltage potential (e.g., "body ground"). For example, in an embodiment, the anchored guide device includes one or more openings that are positioned and sized to expose the cannula to the body wall. In an embodiment, the one or more openings are provided in the side wall of the tube of the guide device, for example at a location that is intended to reside at least partially within the body in an inserted, operational position. In order to prevent insufflation gas from escaping the remote site in the body through the one or more openings during a procedure, the anchored guide device can optionally include a seal, for example, located at or distal to the openings, that seals against the cannula to prevent insufflation gas from escaping around the cannula and through the one or more openings in the anchored guide device.

In various embodiments, the present disclosure contemplates repositionable anchors that can be moved along a tube of the anchored guide device and into position against an outside surface of the body wall. In embodiments, the repositionable anchor is manipulatable by a user with one hand, leaving the user's other hand free to hold and position the anchored guide device.

In further embodiments, the present disclosure contemplates clamping mechanisms at a proximal end of the anchored guide device to grip or otherwise retain the cannula within the tube of the guide device. Clamping mechanisms according to various embodiments can have an unlocked state, in which the cannula can be freely inserted or removed from the tube of the guide device, and a locked state, in which the cannula is securely retained in and prevented from moving relative to the tube of the guide device.

Embodiments disclosed herein are used to position and stabilize a cannula within a body wall during a procedure for accessing a remote site in the body, such as, for example a surgical, treatment, or diagnostic procedure. Embodiments described herein may be used, for example, with teleoperated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture," U.S. Pat. No. 9,295,524 (filed May 31, 2013) to Schena et al., entitled "Redundant Axis and Degree of Freedom for Hardware-Constrained Remote Center Robotic Manipulator," and U.S. Pat. No. 8,852,208 (filed Aug. 12, 2010) to Gomez et al., entitled "Surgical System Instrument Mounting," each of which is hereby incorporated by reference in its entirety. Further, the embodiments described herein may be used, for example, with a da Vinci® Surgical System, such as the da Vinci Si® Surgical System (model no. IS3000) or the da Vinci Xi® Surgical System, both with or without Single-Site® single orifice surgery technology, all commercialized by Intuitive Surgical, Inc. of Sunnyvale, California.

Anchored guide devices according to embodiments of the present disclosure may be used in a component of a trocar assembly. In embodiments, a guide device according to the present disclosure may be used as a cannula to directly receive an instrument to perform a procedure at a remote site. In other embodiments, a guide device of the present disclosure, is designed to itself to receive a cannula, which in turn receives the instrument.

Referring now to FIG. 1, an anchored guide device 100 according to an embodiment of the present disclosure is shown. The anchored guide device 100 comprises a tube 102 having a single wall 104 as indicated by hidden lines. The anchored guide device 100 includes an inflatable member 106 (which may also be referred to as an inflatable anchor) located at a distal end portion 108 of the tube 102. The anchored guide device 100 includes an inlet port 110 at a proximal end portion 112 of the tube 102. An inflation lumen 114 extends through the single wall 104 of the tube 102 and is in fluid communication with the inlet port 110 and the inflatable member 106. Optionally, the inflation lumen 114 is located substantially or entirely within the single wall 104 of the tube 102, as discussed in greater detail below in connection with FIGS. 4-7.

The anchored guide device 100 optionally includes a repositionable anchor member 116 that is movable longitudinally along a length of the tube 102. The repositionable anchor member 116 serves to stabilize the anchored guide device 100 against an outer surface opposite to the surface against which the inflatable anchor 106 engages, such as, for example, e.g., an outer surface of a body wall. Embodiments of anchor member 102 are discussed in greater detail below in connection with FIGS. 13-20.

The tube 102 is formed from a material such as a polymer, a composite material, a metal or metal alloy, or other materials. In some embodiments, the anchored guide device 100 is configured to accept a cannula through the tube 102, and the cannula in turn accepts a tool, such as a surgical instrument (e.g., instrument 1300 discussed in connection with FIG. 25 below). In such embodiments, the anchored guide device 100 optionally comprises a polymer or other non-conductive material and is configured to facilitate an electrically conductive pathway between the cannula and a body wall in which the anchored guide device 100 is inserted. For example, as discussed in connection with FIGS. 10 and 11 below, the anchored guide device 100 optionally includes openings that directly expose the cannula to the body wall.

In other embodiments, the anchored guide device 100 is configured to receive a surgical instrument directly. Stated another way, the anchored guide device 100 itself functions as a cannula to position and support a tool (such as surgical instrument 1300 discussed in connection with FIG. 25 below) during a procedure. In such embodiments, the tube 102 can optionally comprise a conductive material, such as a metal or metal alloy, to facilitate an electrically conductive pathway between the tool and the body wall.

Figure 2:
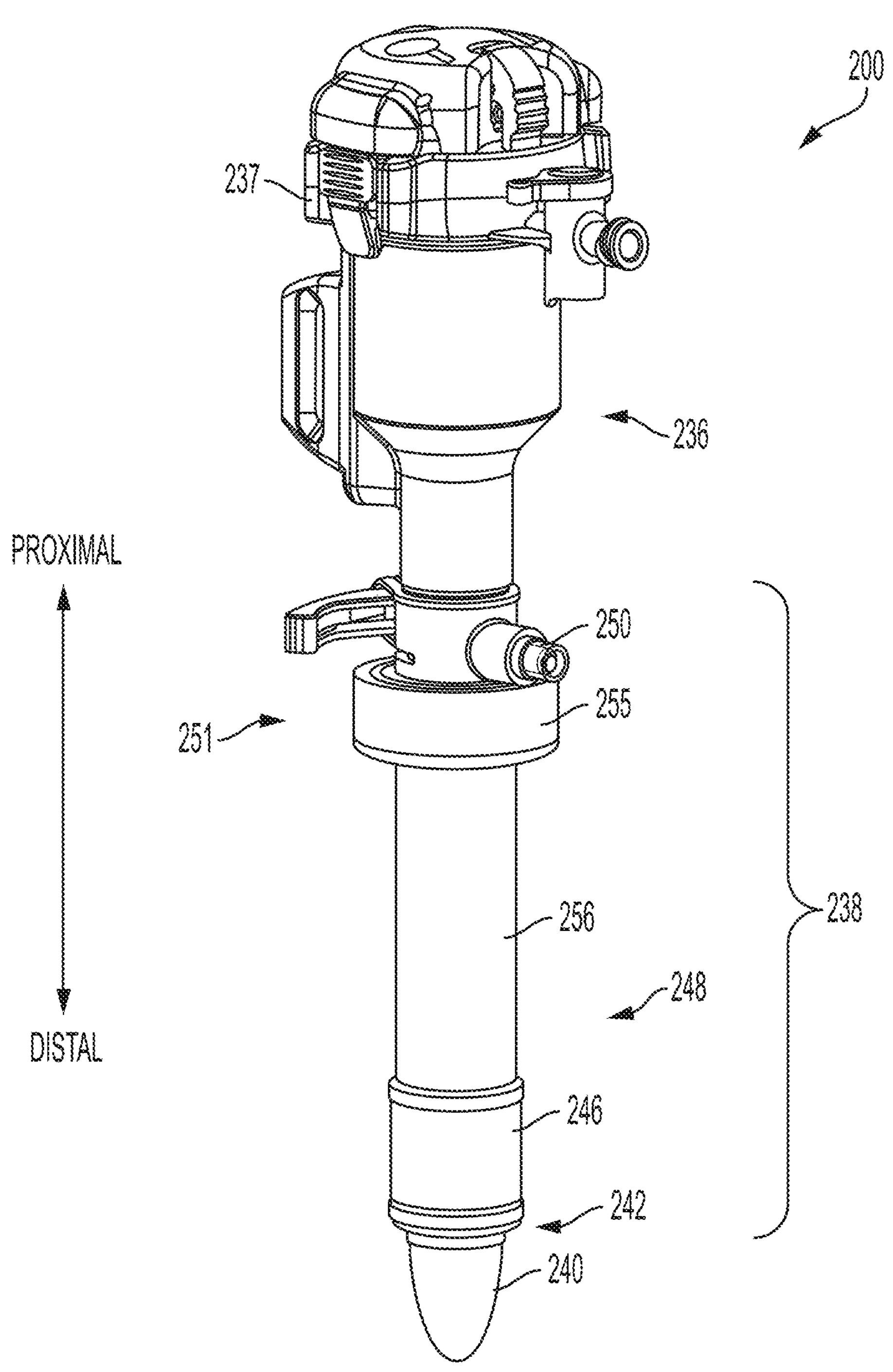
FIG. 2 is a perspective view of an anchored guide device, cannula, seal, and obturator according to the present disclosure.

Referring now to FIG. 2, a perspective view of one embodiment of a trocar assembly 200 according to the present disclosure is shown. The trocar assembly 200 comprises an anchored guide device 238 that includes a tube 256 that is sized and configured to receive a cannula 236 and seal 237 attached. An obturator 240 is insertable through a proximal end of the cannula 236 and extends a length of the cannula such that at least a portion of the obturator extends from a distal end 242 of the tube 256.

The anchored guide device 238 comprises an inflatable member 246 attached at a distal end portion 248 of the anchored guide device 238. An interior chamber (not shown) of the inflatable member 246 is in fluid communication with an inlet port 250 located at a proximal end portion 251 of the anchored guide device 238 through an inflation channel (not visible in FIG. 2; shown and described below with reference to FIGS. 4-7). The anchored guide device 238 further comprises a repositionable anchor member 255 (embodiments of which are discussed in greater detail in FIGS. 13-20 below) that assists in stabilizing the anchored guide device 238 when the device is in use, as discussed further below.

In use, the trocar assembly 200 is introduced into an incision in a body wall. For example, referring to FIG. 3, the anchored guide device 238, optionally a cannula (not shown in FIG. 3), seal, and obturator 240 (not shown in FIG. 3) are inserted as an assembly through an incision 358 in a body wall 360 to a position such that the inflatable member 246 is positioned beyond the body wall 360. The inflatable member 246 is then inflated into an expanded annular shape by introducing air or another fluid through port 250 and along inflation lumen (not shown in FIG. 3) to retain the anchored guide device 238 relative to the body wall 360 and in the incision 358. The repositionable anchor 255 is moved into contact with the body wall 360 to stabilize the anchored guide device 238. The obturator 240 is removed from the anchored guide device 238, and a tool (such as a surgical instrument (not shown)) is then inserted through the anchored guide device 238, or alternatively, through a cannula (not shown) inserted through the anchored guide device 238 to carry out a procedure at a remote site in the body.

Inflation Lumens

Referring now to FIGS. 4-7, depicted are anchored guide devices with various inflation structure arrangements according to various embodiments. In the embodiments of FIGS. 4-7, the anchored guide devices comprise a single-walled tube having an inflation lumen formed by the single wall of the tube. Stated differently, the inflation lumen is a lumen located at least partially between an outer diameter of the single wall and an inner diameter of the single wall. In various embodiments, the inflation lumen comprises a recessed channel formed at least partly by the single-walled tube and one or more components coupled with (e.g., bonded to) the single-walled tube. Alternatively, in other embodiments, the inflation lumen comprises a lumen formed entirely between the outer diameter and inner diameter of the single wall and thus entirely surrounded by the material of the single-walled tube.

Figures 4, 5:
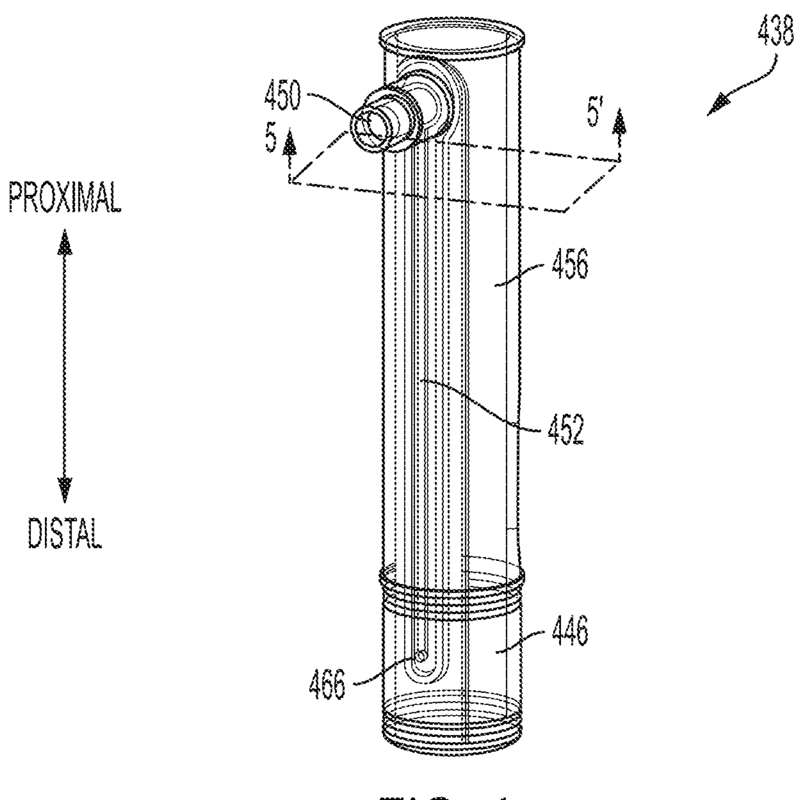
FIG. 4 is a perspective view of an anchored guide device according to the present disclosure.
FIG. 5 is a partial, cross-sectional perspective view of the anchored guide device of FIG. 4.

In various embodiments, the inflation lumen is formed partly as a recessed channel in the single wall of the anchored guide device. In such embodiments, the recessed channel is sealed or otherwise enclosed to form the inflation lumen through the wall of the single-walled tube. For example, referring now to FIGS. 4 and 5, FIG. 4 is a perspective view of an anchored guide device 438 and FIG. 5 is an enlarged cross-sectional view of detail 5-5 of the anchored guide device 438. The anchored guide device 438 includes a recessed channel 452 that is formed on an inside lateral wall 454 of the tube 456 of the anchored guide device 438. The recessed channel 452 comprises a first recess portion 458 having a first width $W_1$ formed in the inside lateral wall 454 of the tube 456, and a second recess portion 460 formed in the wall 454 within the first recess portion 458. The first recess portion 458 and the second recess portion 460 together form the recessed channel 452. As a non-limiting example, a depth $D_1$ of the first recess portion 458 (i.e., a distance from the surface of the inside lateral wall 454 to a bottom surface 455 of the first recess portion 458) can be in a range of from about 0.005 inches (0.127 mm) to about 0.015 inches (0.381 mm). In the embodiment of FIG. 5, $D_1$ is equal to about 0.010 inches (0.254 mm). As a non-limiting example, a depth $D_2$ of the second recess portion 460 (i.e., a distance from the bottom surface 455 of the first recess portion 458 to a bottom surface of the second recess portion 458) can be in a range of from about 0.010 inches (0.254 mm) to about 0.020 inches (0.508 mm). These ranges of values for $D_1$ and $D_2$ are exemplary only, and a person of ordinary skill in the art would understand that values less than or greater than these values are within the scope of the present disclosure.

A total wall thickness T of the tube 456 can be chosen such that a remaining wall thickness $T_r$ between the outer surface of the tube 456 and the bottom surface of the second recess portion 460 is sufficient to facilitate manufacturing of the anchored guide device. For example, in the embodiment of FIGS. 4 and 5, the wall thickness T can be in a range of from about 0.050 inches (1.27 mm) to about 0.1 inches (2.54 mm) or greater. As one example, the thickness T can be chosen relative to $D_1$ and $D_2$ to ensure that at least about 0.024 inches (0.61 mm) thickness $T_r$ remains between the bottom surface of the second recess portion 460 and the outer surface of the tube 456. The dimension of the remaining thickness $T_r$ can be chosen based on a particular manufacturing process used to form the tube 456, such as injection molding, machining, additive manufacturing, or other manufacturing processes, the tolerances associated with the chosen manufacturing process, and/or the material characteristics (such as tensile strength) of the material of the tube 456.

In some embodiments, the depth $D_2$ is greater than half of a wall thickness of the tube 456. In other embodiments, the depth $D_2$ is less than half a wall thickness of the tube. The second recess portion 460 has a width $W_2$, less than the width $W_1$. The recessed channel has a length, measured along an axial direction of the tube 456, that extends between an inlet port 450 and an interior of inflatable member 446. The second recess portion 460 is in fluid communication with the inlet port 250 (FIG. 2) and in fluid communication with the interior of the inflatable member 446.

A cover member 462 is received within and spans the width $W_1$ of the first recess portion 458 to form the inflation lumen 452. Stated differently, the cover member 462 seals the first recess 458 from the interior of the tube 456 to create the inflation lumen 452. A thickness of the cover member 462 is, in some embodiments, similar or equal to the depth $D_1$, such that when the cover member 462 is positioned within the first recess portion 458, the cover member 462 forms a portion of an interior surface of the tube 456 matching or substantially matching an inner diameter of the other portions of the interior surface of the tube 456 to form a generally uniform interior surface of the tube 456.

The cover member 462 can be attached to the tube 456 by, for example and not by way of limitation, laser welding, adhesive bonding, or other techniques. In the embodiment of FIGS. 4 and 5, the cover member 462 is bonded to the tube 456 along a bond bead 464 formed by laser welding. In the embodiment of FIGS. 4 and 5, the bond bead 464 is formed as a continuous loop surrounding the first recess portion 458 and the inlet port 450, and an inflation port 466 that places the inflation lumen 452 in fluid communication with an interior of the inflatable member 446. With the cover member 462 in place, the second recess portion 460 becomes a gas-tight passage between the inlet port 450 and the inflation port 466.

Optionally, the tube 456 comprises a polymer material, such as polyurethane, acrylic, polycarbonate, or another polymer material. In other embodiments, the tube 456 optionally comprises composite materials, a metal, metal alloy, or any other material. Similarly, the cover member 462 may comprise polymer, composite, metallic, or other materials, and may be a similar or dissimilar material to the material of the tube 456.

The tube 456 optionally comprises a partially transparent (e.g., translucent) or fully transparent polymer material. The transparent material enables the cover member 462 to be bonded to the tube 456 by laser welding through the transparent material of the tube 456. In other words, according to some embodiments, to bond the cover member 462 to the tube 456, a laser beam is directed through the exterior of the tube 456 through the translucent material to the cover member 462, fusing (e.g., with or without welding filler material) the material of the cover member 462 and tube 456 together to form a weld (e.g., bond bead 464) between the cover member 462 and the tube 456.

Figure 26:
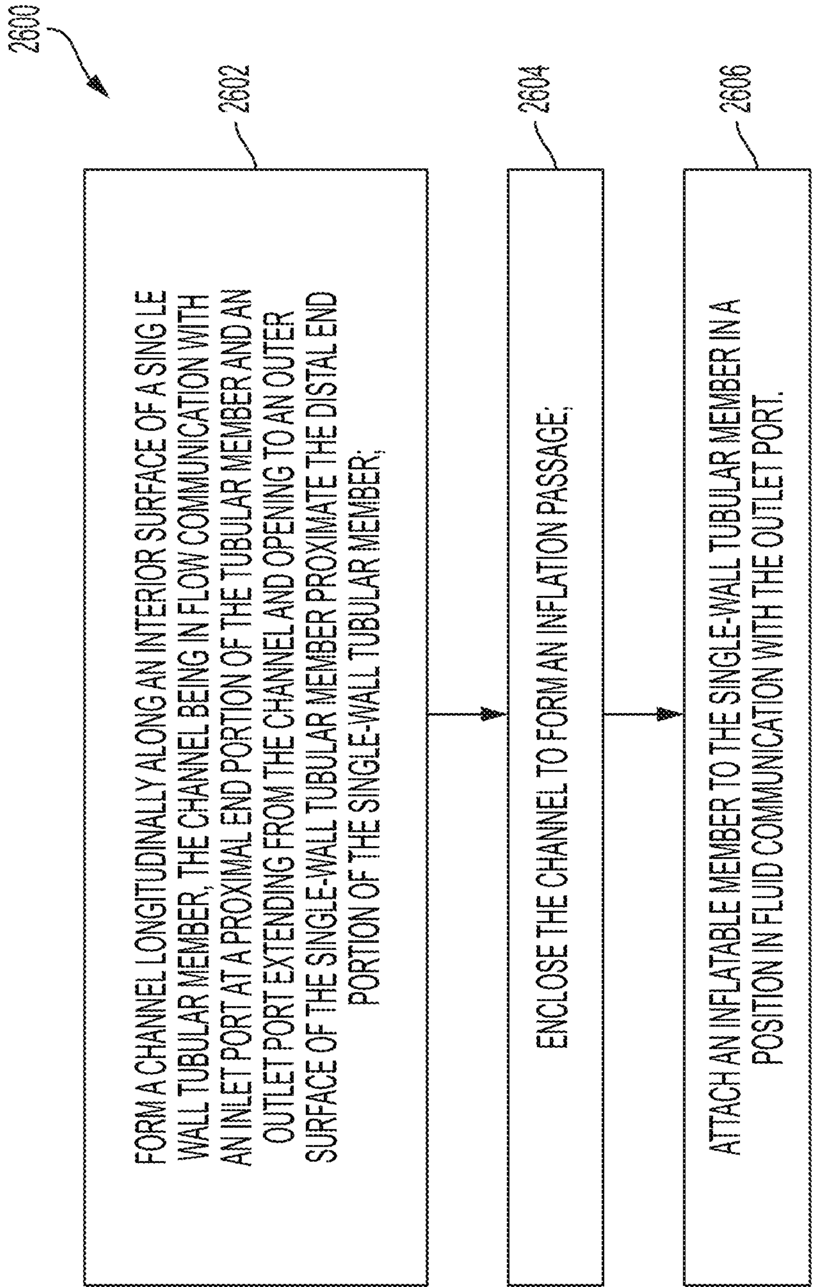
FIG. 26 is a chart showing exemplary items of a workflow for manufacturing an anchored guide device according to the present disclosure.

Referring to FIG. 26, a workflow 2600 for manufacturing an anchored guide device is shown. At 2602, the workflow includes forming a channel longitudinally along an interior lateral wall surface of a single-wall tube. Such a channel can be formed, e.g., by molding, extrusion, additive manufacturing, machining, or any other process. As discussed above in connection with FIGS. 4 and 5, the channel is in flow communication with an inlet port at a proximal end portion of the tube and an outlet port extending from the channel and opening to an outer surface of the single-wall tube proximate the distal end portion of the single-wall tube. At 2604, the workflow includes enclosing the channel to form an inflation lumen. For example, as discussed above in connection with FIGS. 4 and 5, enclosing the channel can optionally include positioning a cover over the channel. Alternatively, the channel may be formed as a full enclosed lumen within the single wall of the tube. At 2606, the workflow includes attaching an inflatable member to the single-wall tube in a position in fluid communication with the outlet port. Attaching the inflatable member to the single-wall tube can be done, for example, as discussed in connection with FIGS. 8 and 9.

In another embodiment of the disclosure, the inflation lumen of the anchored guide device comprises a recessed channel formed in the wall of single-walled tube of the anchored guide device, and a conduit disposed within the channel. For example, referring now to FIGS. 6 and 7, an anchored guide device 538 includes a recessed channel 568 formed in an interior lateral wall surface 554 of single-walled tube of the anchored guide device 538 in a manner similar to inner channel portion 462 of FIGS. 4 and 5. At each end of the recessed channel 568, a lateral passage 569 is formed through the single-walled tube 556 to connect the channel 568 with an inlet port 550 and with an interior of an inflatable member 546, respectively.

Figures 6, 7:
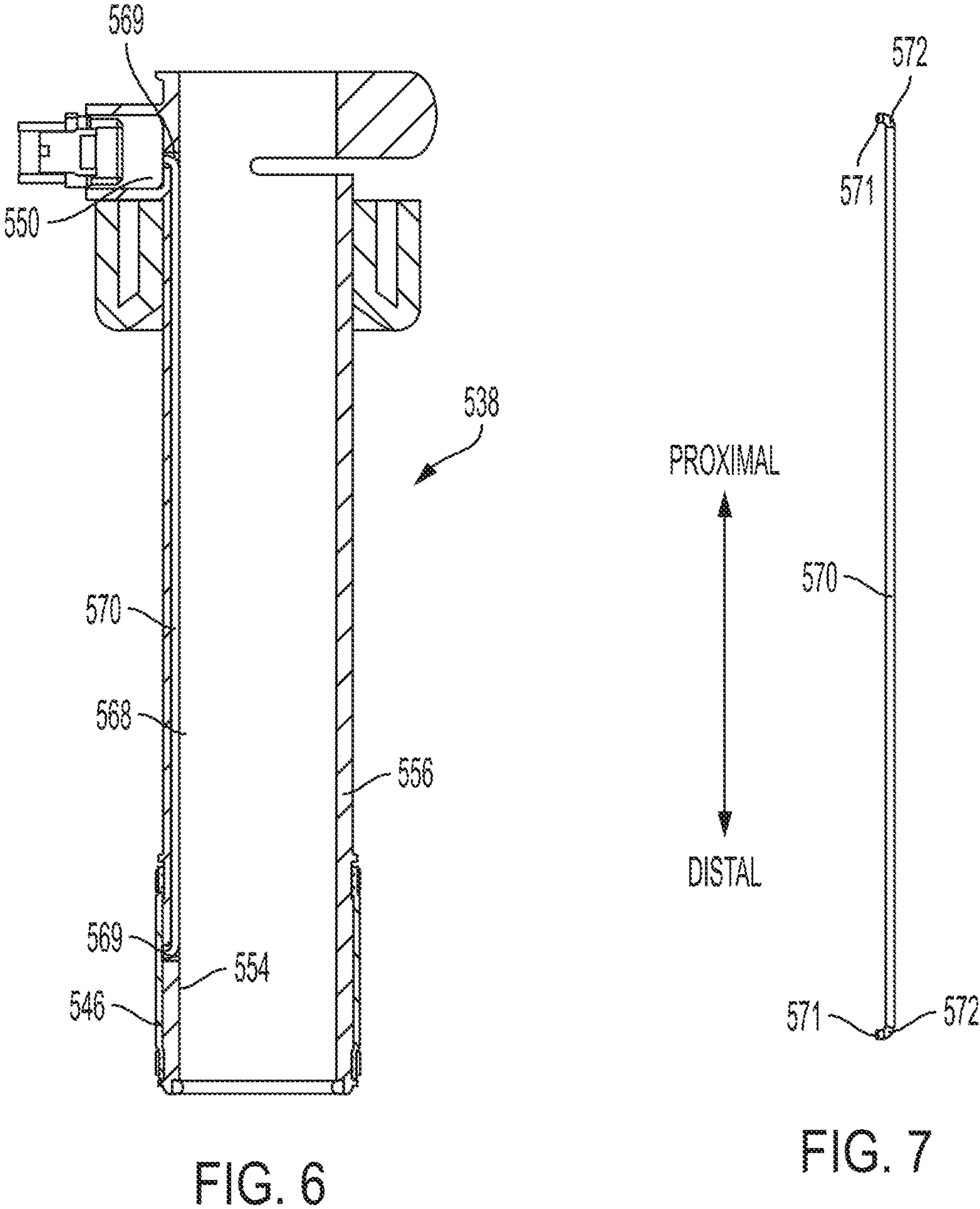
FIG. 6 is a cross-sectional side view of another anchored guide device according to the present disclosure.
FIG. 7 is an enlarged perspective view of an inflation conduit of the anchored guide device of FIG. 6.

A conduit 570 having a size and shape to fit within the recessed channel 568 is placed in the channel 568. The conduit 570 is shown within the channel 568 in FIG. 6 and is shown alone in FIG. 7 to more clearly illustrate the features of the conduit 570. In the embodiment of FIGS. 6 and 7, the conduit 570 comprises bends 572 at each end to permit open ends 571 to fit within lateral passages 569 to allow the conduit 570 to fluidically couple the inlet port 550 to the inflation port. In the embodiment of FIGS. 6 and 7, the bends 572 are angled 90 degrees (i.e., a right angle) but optionally can be angled to a greater or lesser extent. In the embodiment of FIGS. 6 and 7, the conduit 570 has a cross section with a generally annular shape, but the conduit 570 can optionally have any shape that fits within the channel 568. In some embodiments, the conduit 570 is made from a material such as a polymer, a metal or metal alloy, or a composite material. Optionally, the conduit 570 comprises a hypotube, such as a stainless steel hypotube. The hypotube may be bent, for example by mandrel bending or hydroforming, to form the bends 572. In other embodiments, the conduit 570 may comprise a polymer material, and may be molded or otherwise formed to create the bends 572.

In some embodiments, once the conduit 570 is positioned within the recessed channel 568 and the bends 572 and open ends 571 are within the lateral passages 569, the conduit 570 is covered with a filler material (not shown). The filler material can optionally be smoothed to match the contours of the interior lateral wall surface 554 of the single-walled tube, thereby providing a smooth, flush transition between the inner wall and filler material and providing a substantially uniform interior lateral wall surface 554 of the single-walled tube 556. The filler material can further serve to provide a fluidic seal between the single-walled tube 556 and the conduit 570 where the conduit passes through the wall of the single-walled tube 556, such as at lateral passages 569. Thus, the filler material can ensure inflation gas does not leak from the interior of the inflatable member 546. The filler material may comprise, for example, an epoxy or other polymer material, or other materials.

While it may be desirable to have the conduit 570 be flush with the inner surface of the remaining portions of the tube 556, those having ordinary skill in the art would appreciate that the conduit may protrude slightly radially inwardly beyond the inner surface of the tube 556 without departing from the scope of the present disclosure.

Inflatable Member Retention

Figure 3:
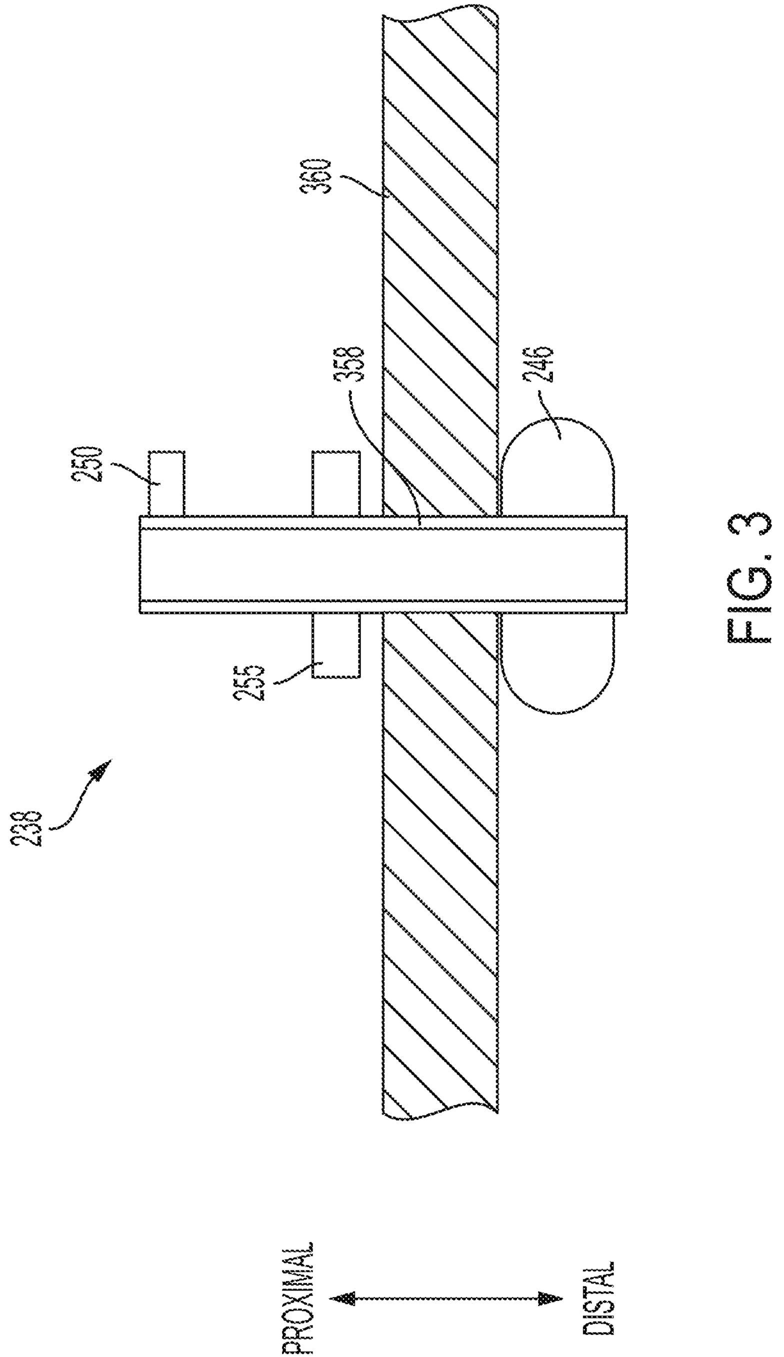
FIG. 3 is a cross-sectional side view of the anchored guide device of FIG. 2, inserted within a body wall.
Figure 8:
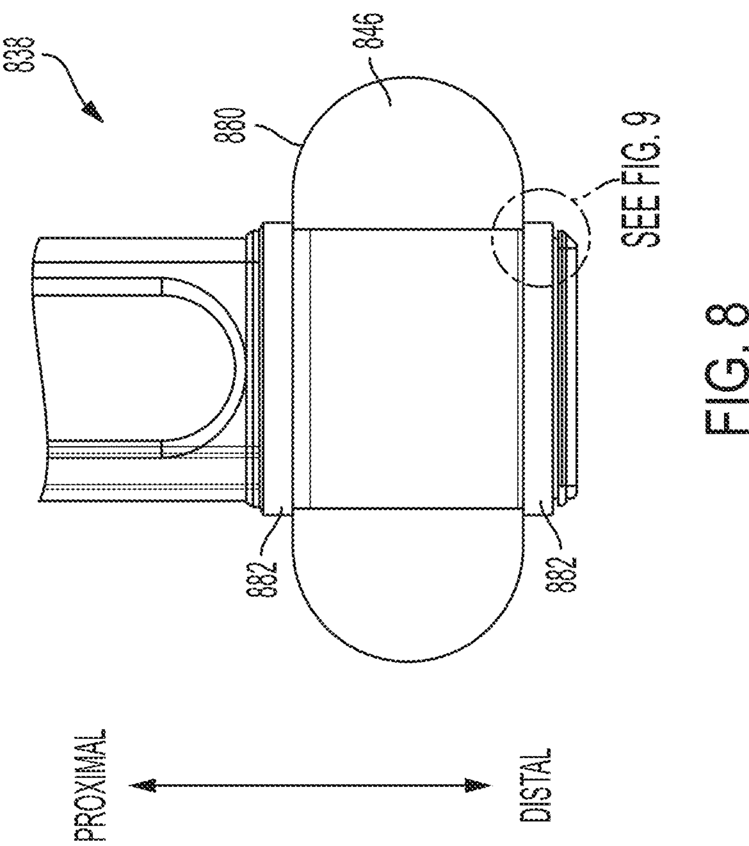
FIG. 8 is a side view of a distal end portion of an anchored guide device according to the present disclosure.

Referring now to FIG. 8, a distal end portion of an anchored guide device 838 is shown with an inflatable member 846 in an inflated and expanded configuration. As shown in FIG. 3, the inflatable member 846 assumes a semi-toroidal shape when inflated. A proximal area 880 of the inflatable member 846 when the inflatable member is in the inflated state engages the body wall to prevent removal of the anchored guide device 838 from an incision through which the anchored guide device 838 is inserted, as discussed in connection with FIG. 3.

The inflatable member 846 is retained on the anchored guide device 838 by, for example, mechanical retention components or by a bond such as an adhesive bond, a weld, or combinations thereof. Mechanical retention components may include, for example, circumferential bands that are placed in a hoop stress condition to maintain the inflatable member 846 on the anchored guide device 838. In the embodiment of FIG. 8, the inflatable member 846 is retained on the anchored guide device 838 by retaining bands 882 positioned at proximal and distal ends of the inflatable member 846. The retaining bands 882 comprise a deformable, ductile material. In an embodiment, the retaining bands 882 have a diameter sufficient to enable the retaining bands 882 to be slipped over the inflatable member 846 when the inflatable member 846 is in place over the anchored guide device 838. After the retaining bands 882 are slipped into position, the retaining bands 882 are subject to a process that reduces the diameter of the retaining bands 882 until the retaining bands 882 are tightened around the inflatable member 846 to retain the inflatable member 846 on the anchored guide device 838.

In the embodiment of FIG. 8, the retaining bands 882 comprise a ductile material such as a metal alloy, for example, stainless steel, or a nickel-titanium alloy (e.g., nitinol). The retaining bands 882 may be reduced in diameter by a process such as swaging with a die, rotary swaging, heat-shrinking (for nickel-titanium alloys) or other techniques. In other embodiments, the retaining bands 882 can optionally be configured to be expanded elastically for positioning over the inflatable member 846, with the elasticity of the retaining bands 882 enabling them to contract over the inflatable member 846 to retain the inflatable member 846 on the anchored guide device 838.

Figure 9:
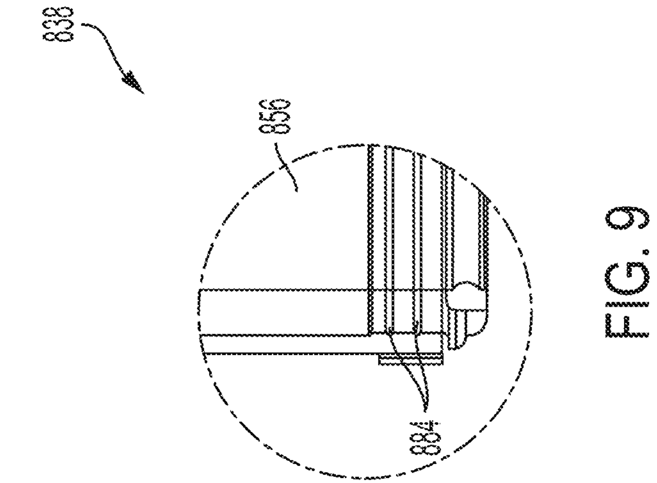
FIG. 9 is a detailed, cross-sectional side view of a portion 9-9 of the distal end portion of the anchored guide device shown in FIG. 8.

The anchored guide device 838 can optionally comprise additional features to prevent the inflatable member 846 from becoming detached from the anchored guide device 838, e.g., by shifting or sliding of the inflatable member 846 under the retaining bands 882. In an embodiment, such features include geometric features of the anchored guide device 838 located underneath the retaining bands 882. For example, referring now to FIG. 9, a detailed view of portion 9-9 of the cross-sectional of FIG. 8 is shown. The anchored guide device 838 includes circumferential ridges 884 formed around the distal end portion of the tube 856 at the location of the retaining bands 882 (only the ridges at the lower retaining bands being depicted, however similar features can be positioned under the proximally disposed retaining band). The circumferential ridges 884 increase holding power of the retaining bands 882 by gripping the inflatable member 846 and preventing the inflatable member 846 from sliding out from under the retaining bands 882. In addition, the circumferential ridges 884 may serve to enhance a gas-tight state between the inflatable member 846 and the tube 856 to prevent escape of inflation gas when the inflatable member 846 is in an inflated state. The circumferential ridges shown in FIG. 9 are one example of various possible features, for enhancing retention of the inflatable member 846. Other embodiments contemplate features such as helical ridges, knurling, or other surface features or patterns to increase surface area contact and gripping of the inflatable member 846.

Structures for Providing Contact Between Cannula and Body Wall

In embodiments of the present disclosure, an anchored guide device may include various features configured to provide an electrically conductive pathway between an electrically conductive portion (e.g., electrically conductive component) of a cannula or other device inserted within the anchored guide device and a body wall (e.g., of a patient). Providing such electrically conductive contact permits the anchored guide device to be made from a non-conductive material, such as, for example, plastic or other composite material. Use of such materials may contribute to efficient molding/manufacturing and/or allow for disposability. Accordingly, various embodiments of the present disclosure include structures that electrically expose the electrically conductive portion of the cannula to a body wall when the guide device and cannula are in an inserted position. For example, in various embodiments, the anchored guide device includes one or more openings extending through a lateral wall of the tube. The one or more openings are arranged and configured to place a portion of a cannula inserted through the anchored guide device in contact with a body wall of a patient. In this way, an electrically conductive portion of the cannula exposed through the one or more openings form a conductive pathway to a body ground (i.e., a voltage potential at which a patient's body is maintained during a surgical procedure). Providing such a conductive pathway may enable reliable shunting of voltage potential of a surgical instrument inserted through the cannula received in the anchored guide device to the body ground. Further, the one or more openings may be dimensioned and arranged to provide a conductive pathway with sufficient contact area to avoid undesirable discharge conditions, such as excess heat and/or discharge through multiple locations.

Figures 10, 11:
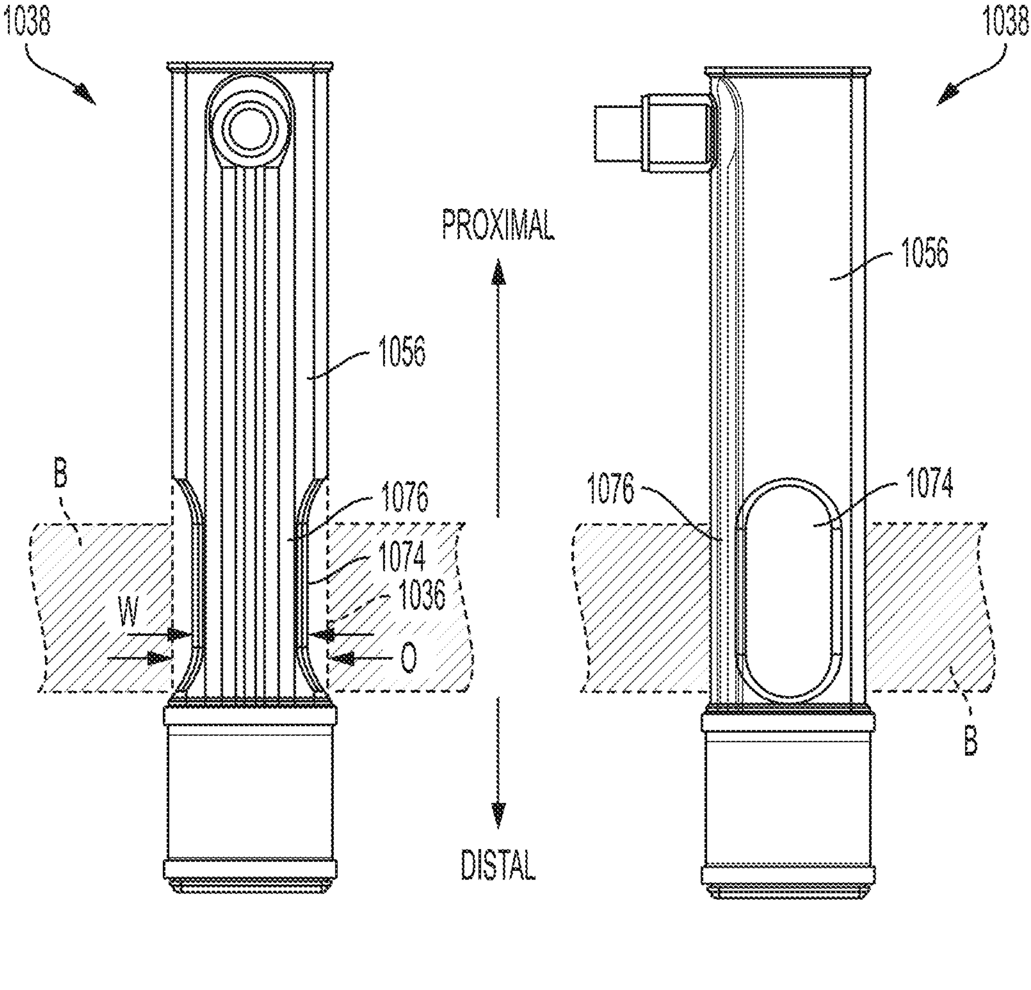
FIG. 10 is a front view of another anchored guide device according to the present disclosure.
FIG. 11 is a side view of the anchored guide device of FIG. 10.

Referring now to FIGS. 10 and 11, an anchored guide device 1038 is shown having a structure similar to that of any of the embodiments described in FIGS. 2-7. However, the anchored guide device 1038 includes one or more openings 1074 extending through the lateral wall of the tube 1056 of the anchored guide device 1038. The one or more openings 1074 may be positioned in the tube 1056 to expose a conducive portion of a cannula or other instrument inserted through the tube 1056 of the anchored guide device 1038 to a body wall B of a patient in which the anchored guide device 1038 is inserted. For example, in the embodiment of FIGS. 10 and 11, the anchored guide device 1138 includes two openings 1074 positioned on diametrically opposite sides of the tube 1056. As shown in FIG. 10, the openings 1074 are generally oval in shape, but optionally can be, for example, round, square, rectangular, elliptical, or any other shape. The openings 1074 are positioned in the tube 1056 directly proximal to the inflatable member 1046 to enhance contact between the cannula (represented by broken lines 1036 in FIG. 10) and the body wall B. The openings 1074 are positioned so that when the anchored guide device 1038 is in an inserted position within the body wall B, with the inflatable member 1146, abutting the internal surface of the body wall B, the openings 1074 are adjacent the body wall B.

The openings 1074 may be configured to maximally expose the conductive portion of the cannula to the body wall B. For example, the one or more openings 1074 can be configured such that a wall of the cannula protrudes beyond a portion of the tube 1056. Referring to FIG. 10, the openings 1074 form an undercut area 1056 around the cannula and expose the cannula beyond the tube 1056. Stated another way, due to the circular cross section of the tube 1056, a portion 1076 of the tube 1056 remaining between the openings 1074 has a linear width W less than a diameter D of a cannula 1036 inserted through the tube 1056. In an embodiment, the width W of the undercut area 1056 is equal to or less than an inner diameter of the tube 1056 defined by an inner surface of the tube 1056. That is, the width W represents a distance between the openings 1074 in a plane P that intersects the opening 1074, the plane P oriented perpendicular to the longitudinal axis $A_L$ of the tube 1056, and the width W can optionally be less than the inner diameter of the tube. Portions of the cannula 1036 thus extend beyond the portion 1076 of the tube 1056 between the openings 1074. This arrangement provides a reliable and consistent electrical pathway between the cannula 1036 and the body wall B.

The anchored guide device 1038 in the embodiment of FIGS. 10 and 11 includes two openings 1074 having an oval shape with a major axis oriented parallel with a length of the tube 1056. In other embodiments, the size, number, and position of the openings 1074 can differ from the embodiments shown herein. For example, other embodiments of anchored guide devices can optionally include one opening, or three or more openings, and the openings can vary in shape and have, for example and not limitation, a circular shape, square shape, rectangular shape, or other shapes and combinations of shapes.

In other embodiments of the disclosure, anchored guide devices can optionally include one or more conductive portions that extend from an interior wall of the tube of the anchored guide device to an exterior wall of the anchored guide device, thereby forming a conductive pathway between the interior and exterior of the tube to provide a shunt to body ground from the conductive portion of the anchored guide device. Such conductive material portions can be used in addition to, or in place of, the one or more openings, and can be positioned, for example, in locations similar to the location of openings 1074. Other positions of the conductive materials are within the scope of the disclosure, and such positions can be chosen to ensure a conductive path between a cannula inserted within the anchored guide tube and a patient's body wall.

Sealing of Anchored Guide Devices

Figure 12A:
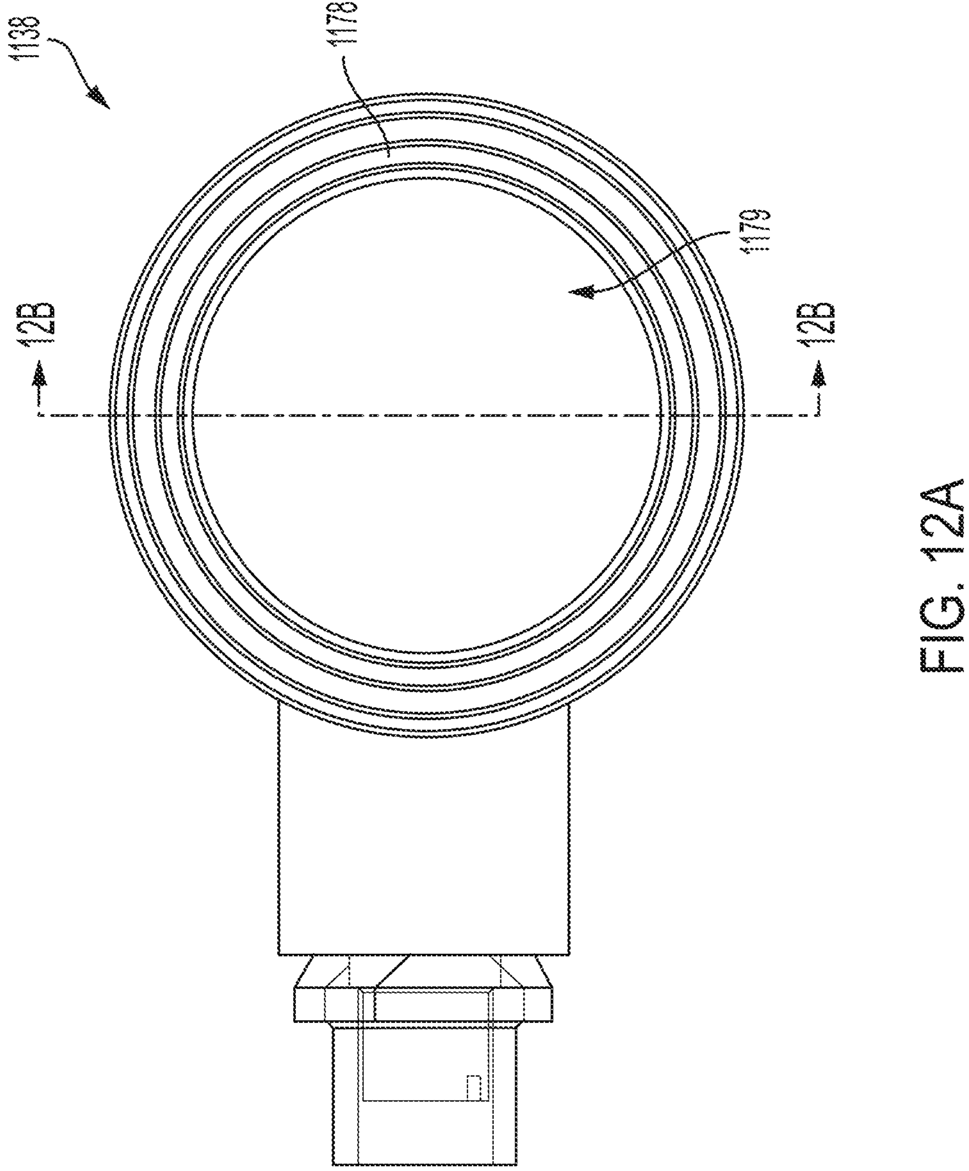
FIG. 12A is a bottom view of a distal end portion of an anchored guide device according to another embodiment of the present disclosure.
Figure 12B:
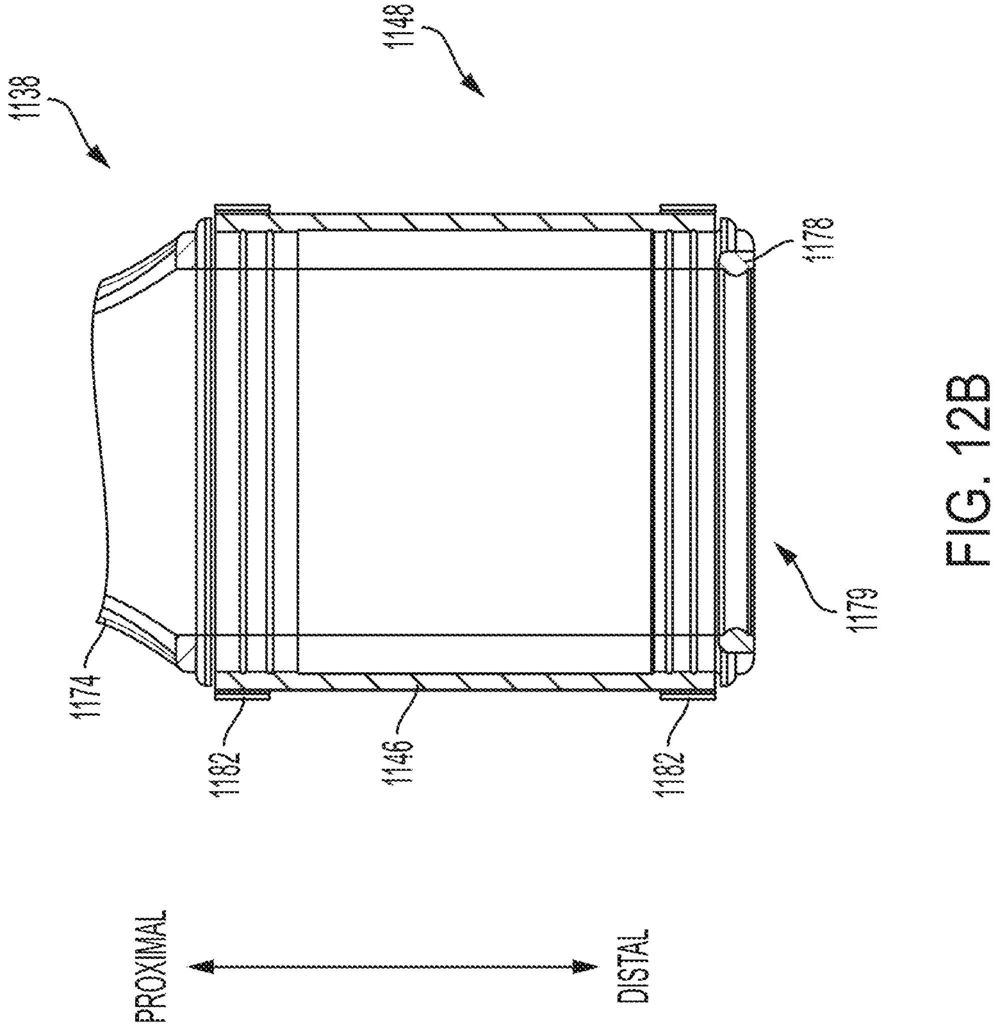
FIG. 12B is a cross-sectional, side view of the distal end portion of the anchored guide device according to FIG. 12A.

In various embodiments, an anchored guide device may be configured to maintain an insufflation pressure at the remote site when the cannula is inserted in an operation position through the anchored guide device. In the embodiment of FIGS. 12A and 12B below, the seal is positioned at a distal end portion of the anchored guide device. In other embodiments, such as embodiments that do not include the openings 1074 (FIGS. 10 and 11), the seal can optionally be positioned at a proximal end of the anchored guide device, or anywhere between the distal end and the proximal end of the anchored guide device.

FIG. 12A shows a bottom view of an anchored guide device 1138 and FIG. 12B shows a cross-sectional view of the anchored guide device 1138 along section B-B. Referring to FIGS. 12A and 12B, a distal end portion of an anchored guide device 1138 comprises a seal member 1178 positioned at a distal end 1048 of the anchored guide device 1138. The seal member 1178 creates a seal between the anchored guide device 1138 and a medical device (e.g., cannula 336) inserted within the anchored guide device 1138 and prevents loss of insufflation gas during a procedure through openings 1174, which may be similar to openings 1074 in FIGS. 10 and 11. Also shown in FIG. 12B are an inflatable member 1146 and retaining members 1182.

The seal member 1178 comprises a resilient material such as, for example, polymers such as silicone rubber, ethylene propylene diene monomer (EPDM), neoprene, or other natural or synthetic polymers, combinations of polymer materials, or other materials. In some embodiments, the seal member 1178 is formed by a process such as injection molding, extrusion, or other processes, and is then bonded (e.g., with an adhesive) to the anchored guide device 1138. In another embodiment, the seal member 1178 is molded onto the anchored guide device 1138 by, e.g., an overmolding process. In some embodiments, the seal member 1178 comprises an O-ring with a round or non-round cross section.

In the embodiment of FIGS. 12A and 12B, the seal member 1178 is positioned at a distal end opening 1179 of the anchored guide device 1138. In other embodiments, the seal member 1178 may be positioned along the anchored guide device 1138 at any axial location distal to the one or more openings in the anchored guide device 1138 (such as, for example, openings 1074 shown in FIGS. 10 and 11) in order to maintain insufflation pressure.

In yet other embodiments, a seal member may be positioned around openings (e.g., around openings 1074 shown in FIGS. 10 and 11) of the tube of the anchored guide device. For example, in an embodiment with two openings, such as openings 1074 in FIGS. 10 and 11, individual seal members can optionally be positioned surrounding each of the openings 1074 on the inside wall of the tube 1056. Embodiments according to the present disclosure can encompass any configuration or shape of seal members that serves to maintain insufflation pressure by preventing an escape of insufflation pressure from the surgical site through the openings in the anchored guide device.

Repositionable Proximal Anchor

As noted above in connection with FIG. 2, the anchored guide device 238 can optionally include a repositionable proximal anchor 255. The repositionable anchor 255 is movable along the tube 256 to a position such that when the anchored guide device 238 is inserted within an incision in a patient's body wall and the inflatable member 246 is in an inflated state, the body wall is sandwiched between the inflatable member 246 and the repositionable anchor 255. The repositionable anchor 255 can optionally include features configured to enhance ease-of-use. For example, features of the repositionable anchor 255 may facilitate a user adjusting the position of the anchor 255 with one hand, while the other hand is free to position and/or stabilize the anchored guide device 238 within the body wall. Additionally, features of the repositionable anchor 255 may facilitate adjusting the position of the repositionable anchor 255 with a minimal effort or movement on the part of the user to manipulate the repositionable anchor 255. The repositionable anchor 255 can also optionally include features configured to facilitate stable contact of the repositionable anchor 255 against the body wall surface.

Figure 13:
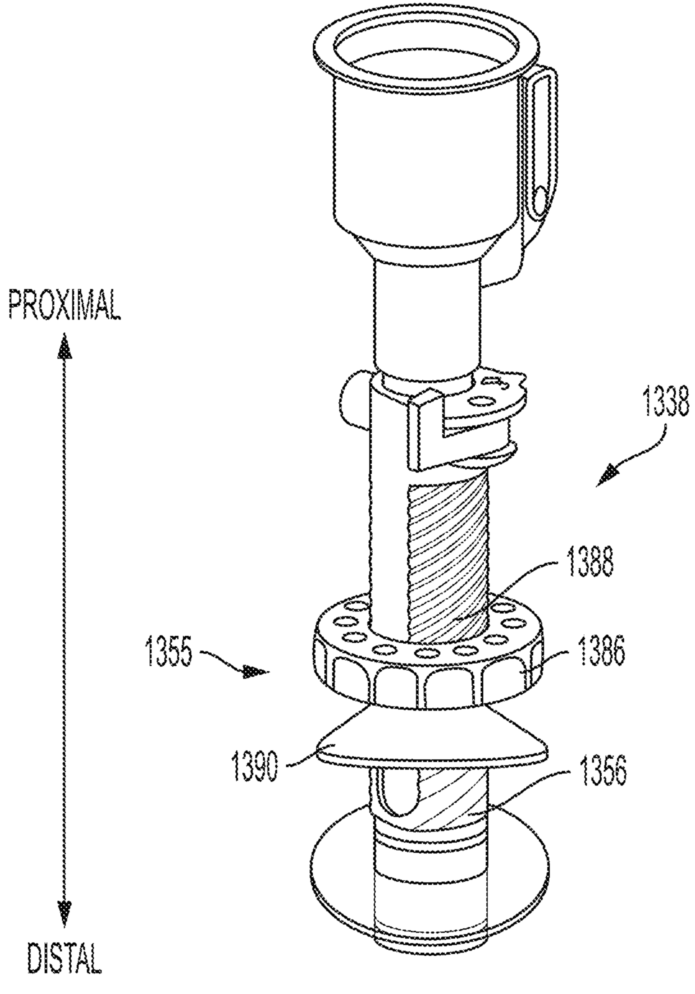
FIG. 13 is a perspective view of another anchored guide device and a cannula according to the present disclosure.

For example, referring now to FIG. 13, an anchored guide device 1338 includes a repositionable anchor 1355 that comprises an internally threaded collar 1386 that engages with threads complementary to external threading 1388 located on an exterior surface of a tube 1356 of the anchored guide device 1338. Various aspects of the threading 1388 (and corresponding internal threading of the collar 1386, not shown in FIG. 13) are chosen to facilitate ease of use of the repositionable anchor 1355. In the embodiment shown in FIG. 13, the pitch of the threading is chosen such that the proximal anchor 1355 moves axially along the tube 1356 device (e.g., in a direction from proximal to distal) a relatively large distance in the axial direction for a given rotation of the proximal anchor 1355. In the embodiment of FIG. 13, the threading has a helix angle in a range of from about 5 degrees to about 45 degrees or more. The threads 1388 may comprise multiple thread leads, such as two thread leads, three thread leads, or more. The relatively high helix angle results in a relatively high lead so as to enable movement of the repositionable anchor 1355 from a proximal-most position on the anchored guide device 1338 to a distal-most position on the anchored guide device 1338 with a relatively low number of turns (e.g., fewer than 5 full turns of the proximal anchor, fewer than 4 full turns, fewer than 3 full turns, etc.).

The proximal anchor 1355 may be made of a material such as silicone rubber, neoprene, or another relatively hard rubber-like material. Suitable materials can contribute to a high coefficient of friction between the internal threading of the collar 1386 and the external threading 1388 of the tube 1356 to prevent the proximal anchor 1355 from loosening once the user places the proximal anchor 1355 in the desired position.

The proximal anchor 1355 can optionally include features on a distal portion that are configured to provide stable contact between the proximal anchor 1355 and the body wall. For example, as shown in FIG. 13, the proximal anchor 1355 includes a flange 1390 configured to rest against the body wall and provide a greater contact area with the body wall than would be provided by the proximal anchor 1355 in the absence of the flange 1390. The flange 1390 can optionally comprise geometry and/or material that imparts flexibility to the flange 1390, thereby facilitating the flange 1390 deforming to match contours of the patient's body wall. In other embodiments, the proximal anchor 1355 may include other features, such as a Hassan cone, as described in Intl Patent App. Pub. No. WO 2016/196276 A2 (filed May 27, 2018), and titled "CANNULA FIXATION DEVICES, SYSTEMS, AND RELATED METHODS, the entire contents of which are incorporated by reference herein.

In some embodiments, the repositionable anchor comprises features that selectively engage engagement features of the anchored guide device tube to maintain the repositionable anchor in a desired position. The repositionable anchor may be configured to be manipulated by a user to selectively engage or release the repositionable anchor features from the tube of the anchored guide device. The guide device can have a first configuration in which the anchor is movable (e.g., translatable) along the tube, and a second configuration in which the anchor is fixed (e.g., fixed in translation) relative to the tube.

Figures 14, 15:
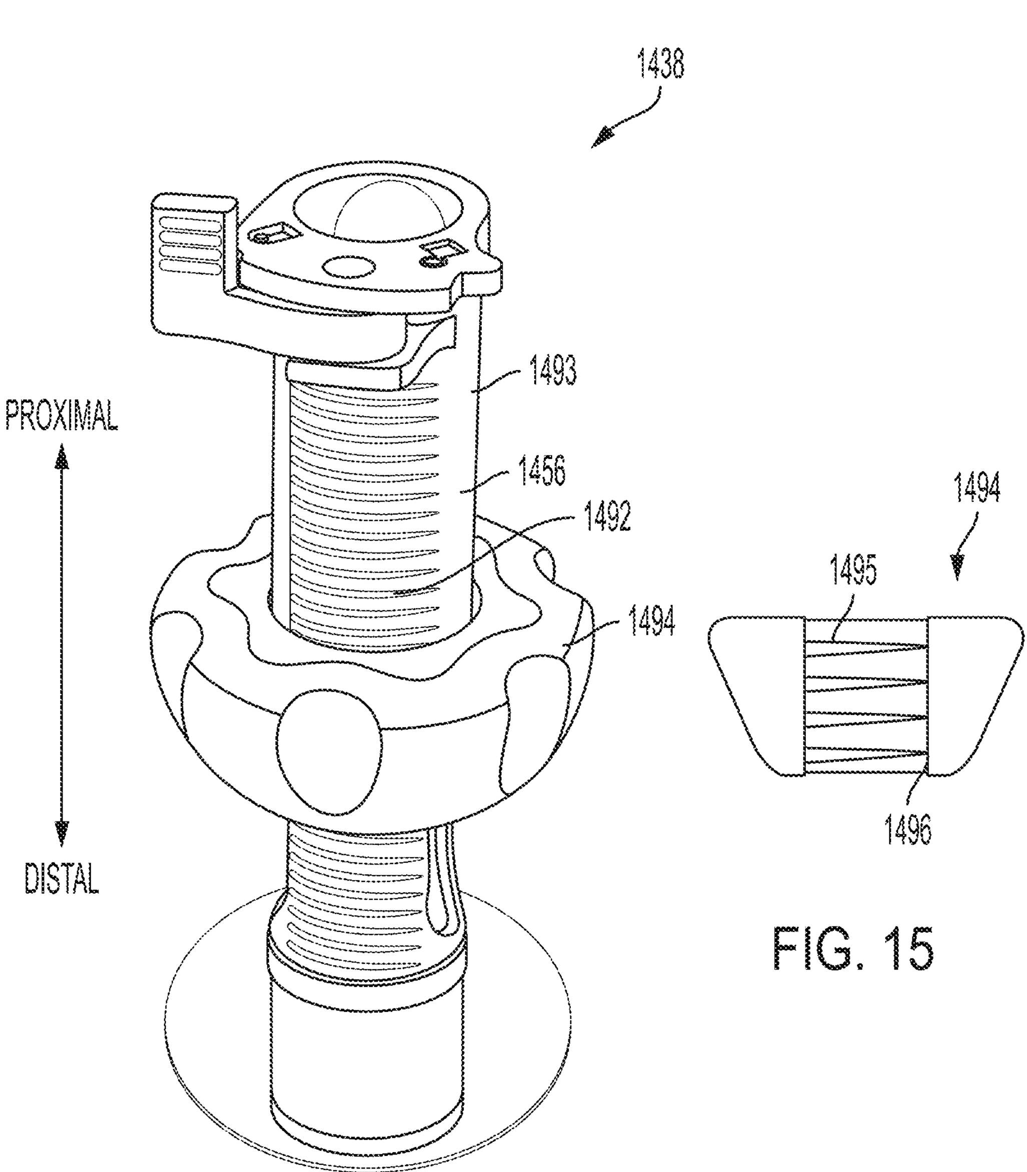
FIG. 14 is a perspective view of another anchored guide device of the present disclosure.
FIG. 15 is a longitudinal, cross-sectional view of a repositionable anchor according to the present disclosure.

For example, referring now to FIG. 14, another embodiment of a proximal repositionable anchor of an anchored guide device 1438 is shown. In the embodiment of FIG. 14, a tube 1456 of the anchored guide device 1438 includes a series of tapered teeth 1492 on an exterior surface of the tube 1456. The tapered teeth 1492 extend in a generally circumferential direction around the tube 1456. The tube 1456 includes smooth areas 1493 along the length of the tube 1456 that circumferentially separate sets of tapered teeth 1492. While not shown in the view of FIG. 14, the tube 1456 includes a series of tapered teeth 1492 that are positioned diametrically opposite the tapered teeth 1492. A repositionable anchor 1494 includes corresponding complementary internal teeth 1495 (shown in FIG. 15) on a sidewall of a bore 1496 of the repositionable anchor 1494. The tapered teeth 1492 can be engaged with the corresponding complementary internal teeth 1495 by rotation (e.g., a quarter turn) of the repositionable anchor 1494 relative to the tube 1456 to hold the repositionable anchor 1494 in place along the tube 1456. Likewise, the repositionable anchor 1494 can be disengaged and moved longitudinally along the tube 1456 by rotating the repositionable anchor 1494 (counter clockwise, as viewed from the proximal end in the embodiment of FIG. 14) so that the internal teeth 1495 are disengaged from the tapered teeth 1492 and aligned with the smooth areas 1493 of the tube 1456. In this manner, a user can quickly slide the repositionable anchor 1494 to a desired position along a length of the tube 1456 to stabilize the anchored guide device 1438 within an incision in a patient's body wall and can lock the repositionable anchor 1494 in place with a partial (e.g., quarter) rotation to engage the internal teeth 1495 with the tapered teeth 1492.

Figure 16:
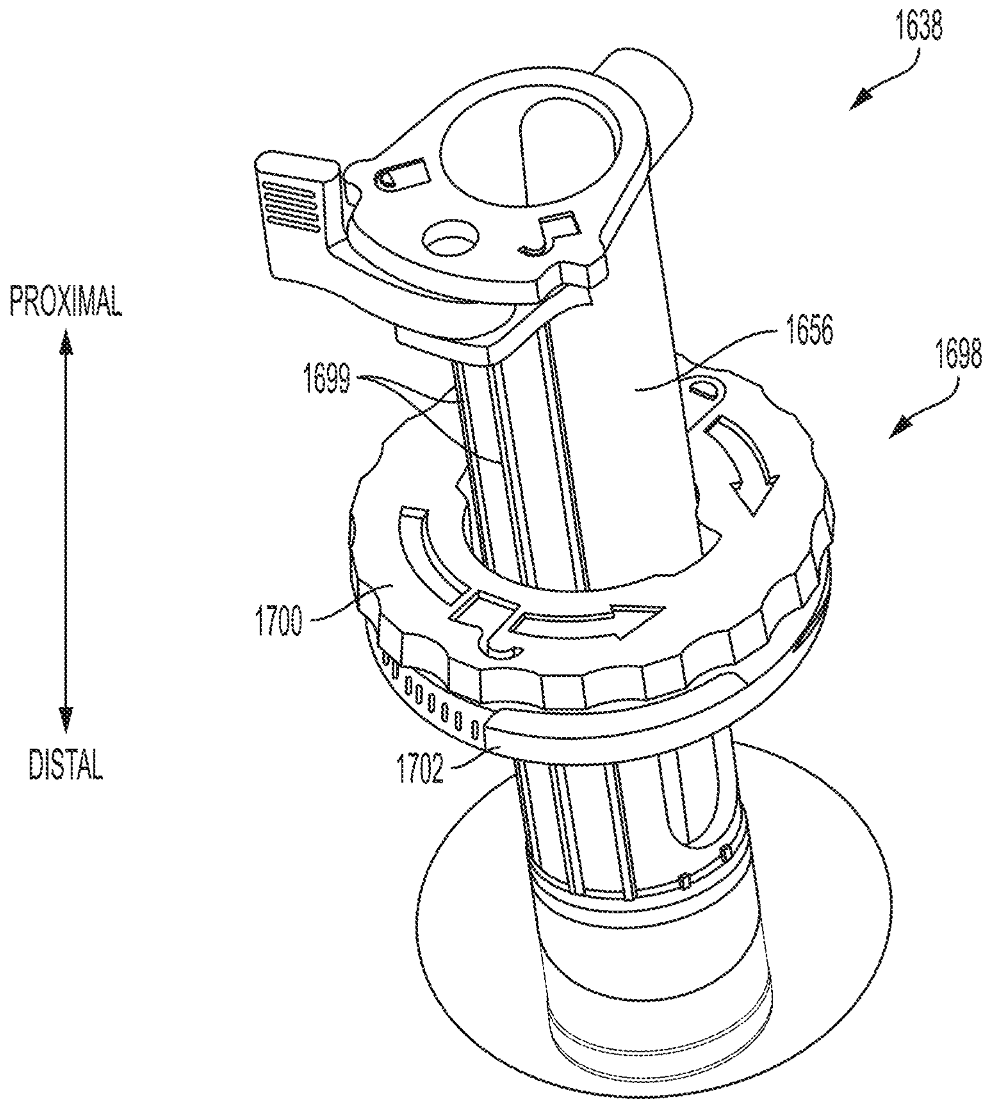
FIG. 16 is a perspective view of an anchored guide device according to the present disclosure.
Figures 17A, 17B:
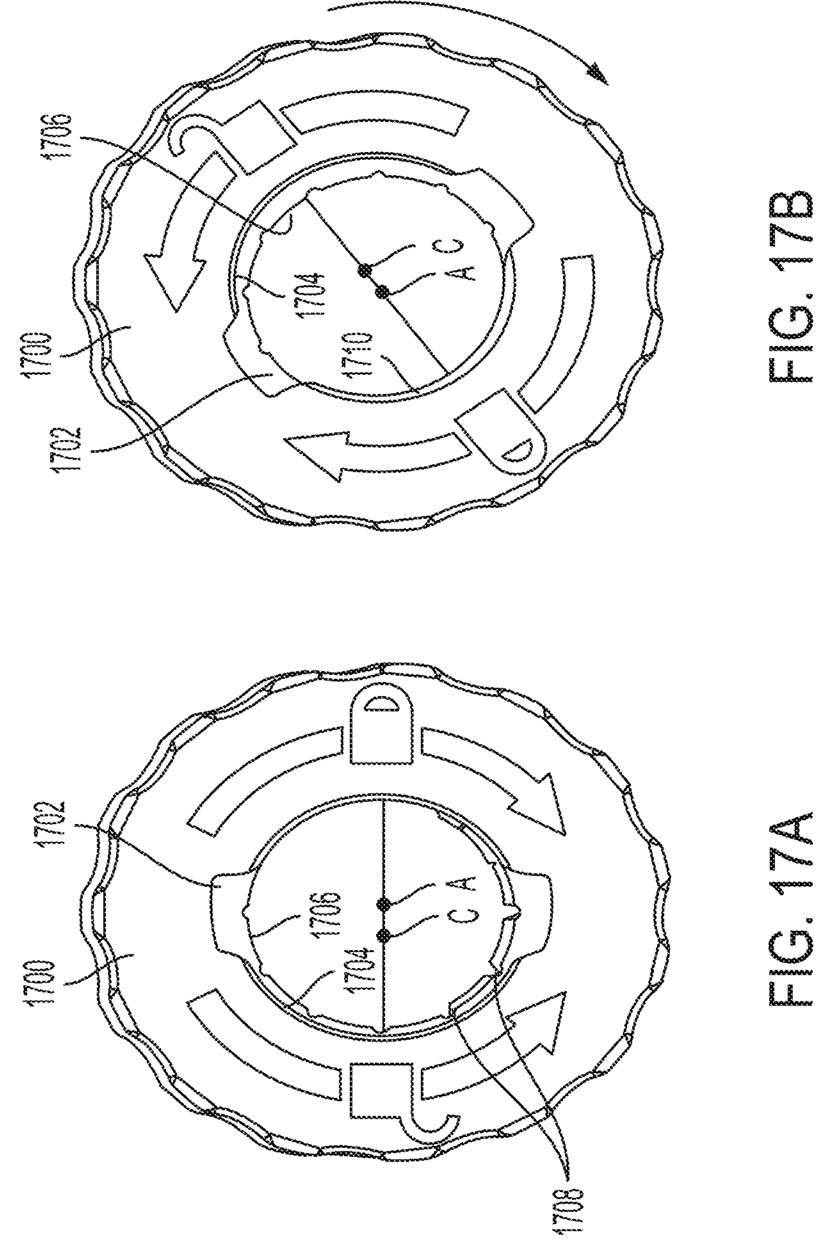
FIG. 17A is a top view of a repositionable anchor in an unlocked position according to the present disclosure.
FIG. 17B is a top view showing the repositionable anchor of FIG. 17A in a locked position.

Referring now to FIGS. 16, 17A, and 17B, another embodiment of an anchored guide device 1638 with a repositionable proximal anchor 1698 is shown. In this embodiment, the repositionable anchor 1698 comprises a two-piece, eccentric design that clamps a tube 1656 of the anchored guide device 1638 in a locked position and releases the tube 1656 in an unlocked position to enable sliding the repositionable anchor 1698 along a length of the tube 1656.

In this embodiment, the repositionable anchor 1698 comprises a first collar 1700 and a second collar 1702. The first collar 1700 is positioned proximal to the second collar 1702. Referring now to FIGS. 17A and 17B, the first collar 1700 comprises a bore 1704 with a central axis C offset from a rotational axis A of the first collar 1700. The rotational axis A of the first collar is coaxial with a central axis of a bore 1706 of the second collar 1702. The first collar 1700 is rotatably coupled with the second collar 1702.

In the unlocked position shown in FIG. 17A, the bore 1704 of the first collar is generally coaxial with the bore 1706 of the second collar 1702. When the first collar 1700 is rotated relative to the second collar 1702, because the rotational axis A of the first collar 1700 is offset relative to the central axis C of the bore 1704 of the first collar 1700, the bore 1704 moves from a coaxial position with the bore 1706 of the second collar 1702 to an offset position with respect to the bore 1706 of the second collar 1702.

The second collar 1702 includes grooves 1708 in the bore 1706 that receive longitudinal ridges 1699 (shown in FIG. 16) on the tube 1656 and prevent rotation of the second collar 1702 relative to the tube 1656. The longitudinal ridges 1699 can also be referred to herein as "engagement features." When a user rotates the first collar 1700 clockwise as viewed in the plane of FIGS. 17A and 17B, the bore 1704 of the first collar becomes offset relative to the bore 1706 of the second collar 1702, and a sidewall 1710 of the bore 1704 partially obscures the bore 1706 of the second collar 1702, effectively reducing a diameter of the bore 1706 and clamping the tube 1656 within the repositionable anchor 1698 (see FIG. 16). Friction between the tube 1656, the bore 1704 of the first collar 1700, and the bore 1706 of the second collar 1702 hold the repositionable anchor 1698 in place along the tube 1656.

To release repositionable anchor 1698, the user rotates the first collar 1700 counterclockwise (in the view of FIGS. 17A and 17B), and the bore 1704 of the first collar returns to a coaxial position relative to the bore 1706 of the second collar, and the tube 1656 is released and the unlocked proximal anchor 1698 can be freely moved along the tube 1656.

In yet other embodiments, an anchored guide device includes a repositionable anchor with features configured to selectively engage with engagement features of the anchored guide device tube to selectively retain the proximal anchor in a desired location along the length of the anchored guide device. In some embodiments, a component of the repositionable anchor comprises one or more resilient portions that enable selective engagement and disengagement of the releasable pawls with teeth on the tube of the anchored guide device based on a user's application of force to the repositionable anchor.

For example, referring now to FIGS. 18 through 20, an embodiment of an anchored guide device 1838 with a ratcheting repositionable proximal anchor 1810 is shown. Referring now to FIG. 18, the repositionable anchor 1810 includes at least one ratchet pawl 1812 configured to engage ratchet teeth 1814 on the tube 1856 of the anchored guide device 1838. Each of the ratchet teeth 1814 on the tube 1856 have an angled portion 1813 facing generally proximally (i.e., upward in the orientation of FIG. 18) and a flat portion 1815 facing distally (i.e., downward in the orientation of FIG. 18). The repositionable anchor 1810 also includes at least one release actuator 1816 configured to be manipulated by user of the anchored guide device to selectively release the ratchet pawl 1812 from engagement with the ratchet teeth 1814. In the embodiment of FIGS. 18-20, the repositionable anchor 1810 includes two ratchet pawls 1812 positioned radially opposite one another around the tube of the anchored guide device, and two release actuators 1816 positioned radially opposite one another and at right angles to the two ratchet pawls 1812.

The repositionable anchor 1810 includes resilient portions 1818 connecting the ratchet pawls 1812 and the release actuators 1816. To position the repositionable anchor 1810, the user presses the proximal anchor in a distal direction (i.e., downward toward the inflatable member 1846 in the orientation of FIG. 18). This causes the ratchet pawls 1812 to ride up on the angled portions 1813 of the teeth 1814, enabling the repositionable anchor 1810 to be pushed in the distal direction. The repositionable anchor 1810 is prevented from moving back in the proximal direction by the ratchet pawls 1812 engaging the flat portion 1815 of the teeth 1814, thus providing the "ratcheting" action of the repositionable anchor 1810.

To release the repositionable anchor 1810, force is applied to the release actuator 1816, e.g., by gripping and squeezing the release portions 1816 together around the tube 1856. When the release portions 1816 are pressed inward toward the tube 1856, the resilient portions 1818 flex and the ratchet pawls 1812 move away from the tube 1856, releasing the ratchet pawls 1812 from the flat portions 1813 of the teeth 1814, thereby allowing the proximal anchor 1810 to move proximally along the tube 1856. In some embodiments, the distal side 1820 of the repositionable anchor 1810 features a Hassan cone profile, as described in detail in Intl Patent App. Pub. No. WO 2016/196276 A2, incorporated above.

Proximal Latch Mechanism

Anchored guide devices according to various embodiments of the disclosure can include devices configured to selectively couple a cannula (such as cannula 236 shown in FIG. 2) with the anchored guide device. For example, in some embodiments, an anchored guide device includes an actuatable clamping mechanism at the proximal end of the tube. The clamping mechanism may include one or more features configured to retain the cannula in the anchored guide device through mechanical contact (e.g., an interference fit) between the clamping mechanism and the cannula. The clamping mechanism may include a feature, such as a lever, configured to be manipulated by the user to change the clamping mechanism from a closed position, in which the cannula is retained within the tube of the anchored guide device, and an open position, in which the cannula is free to be removed from the anchored guide device.

Referring now to FIGS. 21A and 21B, a top view of an anchored guide device 2136 (i.e., a view looking down on the proximal end of the anchored guide device 2136) is shown. The anchored guide device 2136 includes a clamping mechanism 2122 at the proximal end. The clamping mechanism 2122 comprises a lever 2124 sized and positioned to be manipulated by a user of the anchored guide device 2136. The lever 2124 is movable between an open position as shown in FIG. 21A and a closed position, as shown in FIG. 21B. In the closed position, an eccentric cam 2126 protrudes into the bore 2128 of the tube of the anchored guide device 2136. The protrusion of the cam 2126 into the bore 2128 contacts a cannula (not shown) inserted within the bore 2128 sandwich the cannula between a wall of the bore 2128 and the eccentric cam 2126, thereby retaining the cannula within the anchored guide device 2136.

Referring now to FIGS. 22A and 22B, a sectional end view of the anchored guide device 2136 taken through the clamping mechanism 2122 is shown to more clearly illustrate the eccentric cam 2126. In the open position shown in FIG. 22A, the eccentric cam 2126 is positioned outside the bore 2128 and allows a cannula to be freely inserted and withdrawn. In the closed position of FIG. 22B, the eccentric cam 2126 partially protrudes into the bore 2128, thereby creating the interference fit between the cannula (not shown), the bore 2128, and the eccentric cam 2126, as discussed above, to retain the cannula in position within the bore 2128.

Figure 23:
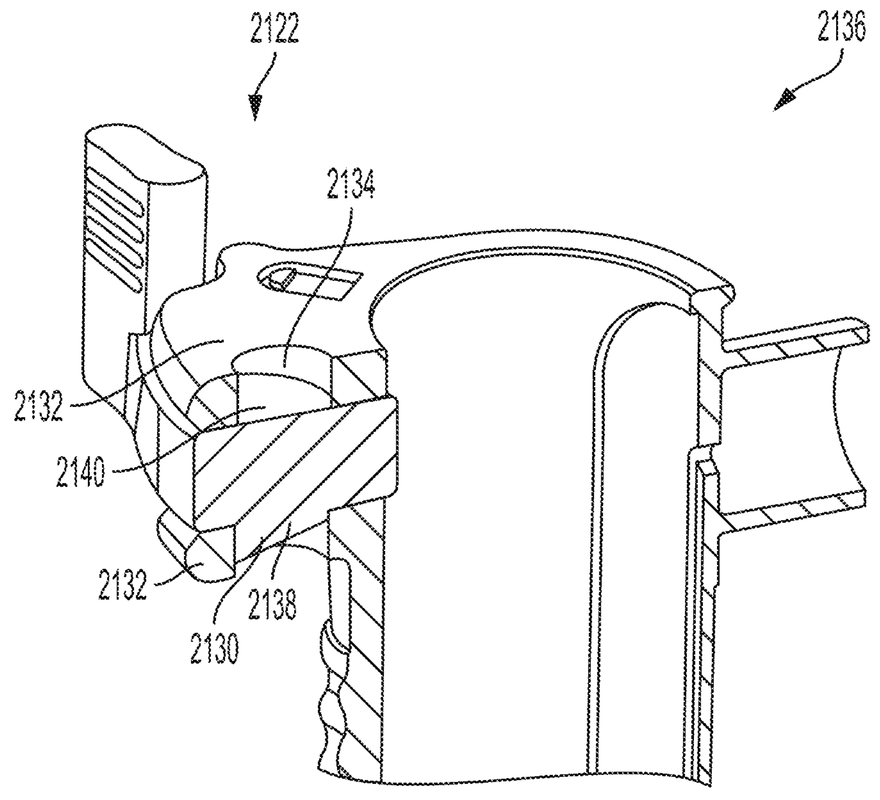
FIG. 23 is a cut-away, perspective view of the proximal latch device and a portion of the anchored guide device of FIG. 22A in the locked position.

Referring now to FIG. 23, a perspective, cross-sectional view of the clamping mechanism 2122 of the anchored guide device 2136 is shown. The clamping mechanism 2122 includes a pin 2130 that retains the clamping mechanism 2122 between flanges 2132 of the anchored guide device 2136. The pin 2130 rides within holes 2134 in the flanges 2132 to enable rotation of the clamping mechanism 2122 between the closed and open positions described in connection with FIGS. 21A-22B.

The pin 2130 features a bevel 2138 that facilitates assembly of the latching mechanism 2122 between the flanges 2132, i.e., by elastic deformation of the flanges 2132. For example, the bevel 2138 imparts to the pin 2130 a generally wedge-shaped profile (as viewed in the orientation of FIG. 23) that serves to gradually spread the flanges 2132 apart to accept the latching mechanism 2122. Once the pin 2130 enters the holes 2134 in the flanges 2132, the flanges 2132 return to an undeformed position to retain the latching mechanism 2122 on the anchored guide device 2136. The bevel 2138 of the pin 2130 creates a shoulder portion 2140 that ensures the pin 2130 remains engaged within the holes 2134 when the latching mechanism 2122 is moved from the open position (as shown in FIG. 21A) to the closed position (as shown in FIG. 21B). In particular, the shoulder portion 2140 contacts the holes 2134 opposite the eccentric cam 2126 to ensure the latching mechanism 2122 is retained in position between the flanges 2132.

Other arrangements and configurations of latching mechanisms are within the scope of the disclosure. For example, a latch device can optionally comprise a clamping element such as a split collar or other mechanical retaining device.

Figure 24:
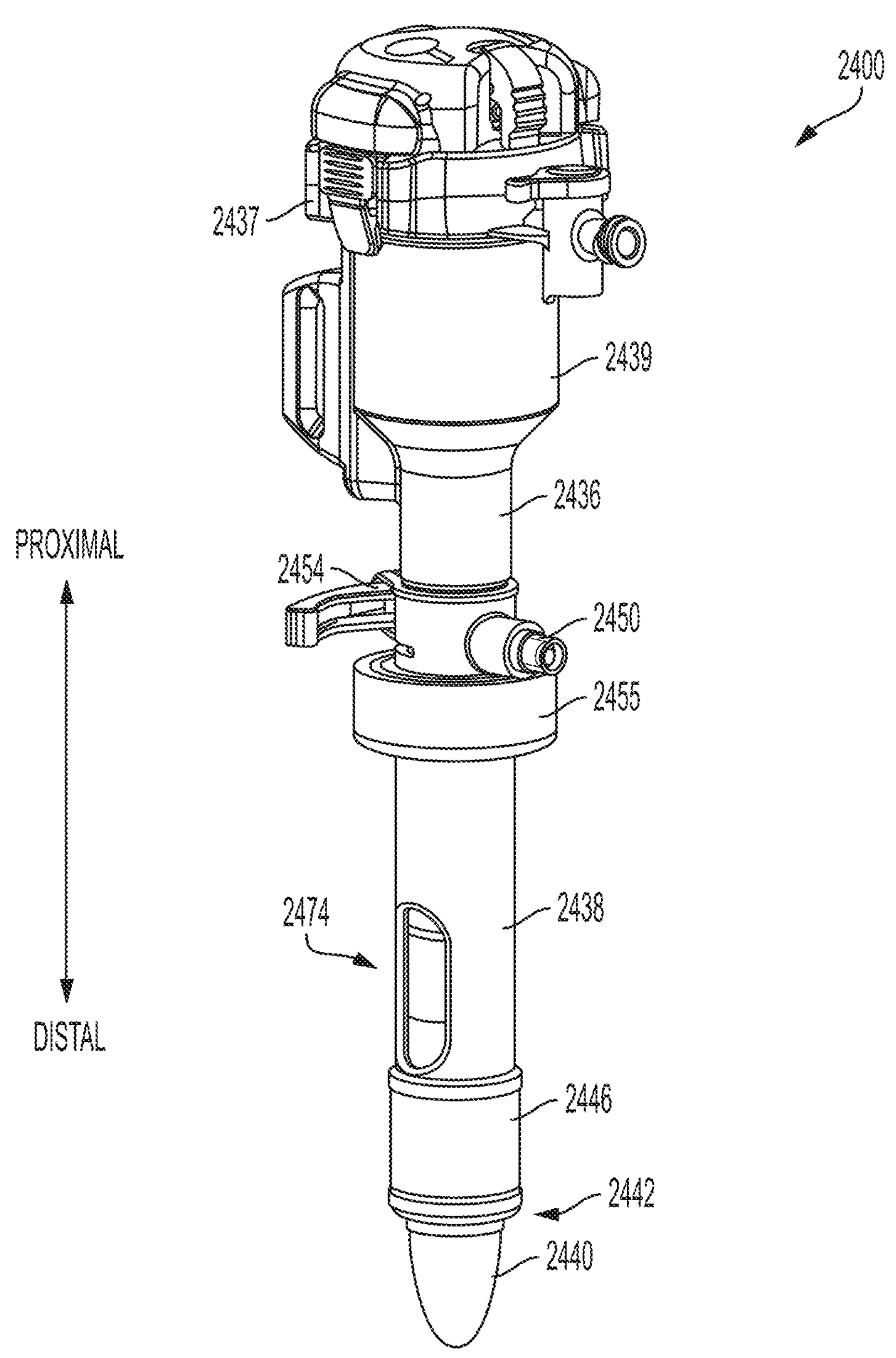
FIG. 24 is a perspective view of an anchored guide device, obturator, seal, and cannula (trocar assembly) according to the present disclosure.

Referring now to FIG. 24, a trocar assembly 2400 according to an embodiment is shown. The trocar assembly 2400 includes an anchor guide device 2438, a cannula 2436 disposed within the anchor guide device 2438, and an obturator 2440 is disposed within the cannula 2436. A proximal end seal member 2437 is coupled with a proximal end of the cannula 2436. In the embodiment of FIG. 24, the obturator 2440 is coupled to the proximal end seal member 2437 and extends a length of the cannula such that a least a portion of the obturator 2440 extends from a distal end 2442 of the anchor guide device 2438. In the embodiment of FIG. 24, the proximal end of the cannula 2436 comprises a cannula bowl 2439. The cannula 2436 is retained in the anchor guide device 2438 by a proximal latch 2454. The anchor guide device 2438 includes an inflatable member 2446 and a repositionable anchor 2455 movable along the length of the anchor guide device 2438. Openings 2474 in the anchor guide device 2438 expose the cannula 2436 to a body wall in which the trocar assembly 2400 is positioned.

In use, the trocar assembly 2400 is inserted within an incision in a body wall, e.g., as shown in FIG. 3. The inflatable member 2446 is inflated by a supply of gas through inlet port 2450 to retain the anchor guide device 2438 within the body wall, and the repositionable anchor 2455 is moved into contact with the body wall to stabilize and position the anchor guide device 2438. The obturator 2440 is then removed from the cannula 2436. A tool, such as a surgical instrument, is then inserted through the cannula 2436 to perform a procedure, while the inflatable member 2446 and repositionable anchor 2455 retain and maintain the position of the anchor guide device 2438 within the body wall.

Embodiments of the present disclosure can be used with various tools, such as surgical instruments and related systems. For example, referring to FIG. 25, one embodiment of a manipulating system 1000 of a teleoperated, computer-assisted surgical system with which embodiments of an anchored guide device according to the present disclosure may be used is shown. Such a surgical system may further include a surgeon console (not shown) for receiving input from a user to control instruments of manipulating system 1000, as well as an auxiliary system (not shown), as described in, for example, U.S. Pat. Nos. 9,358,074 and 9,295,524, incorporated by reference above.

Figure 25:
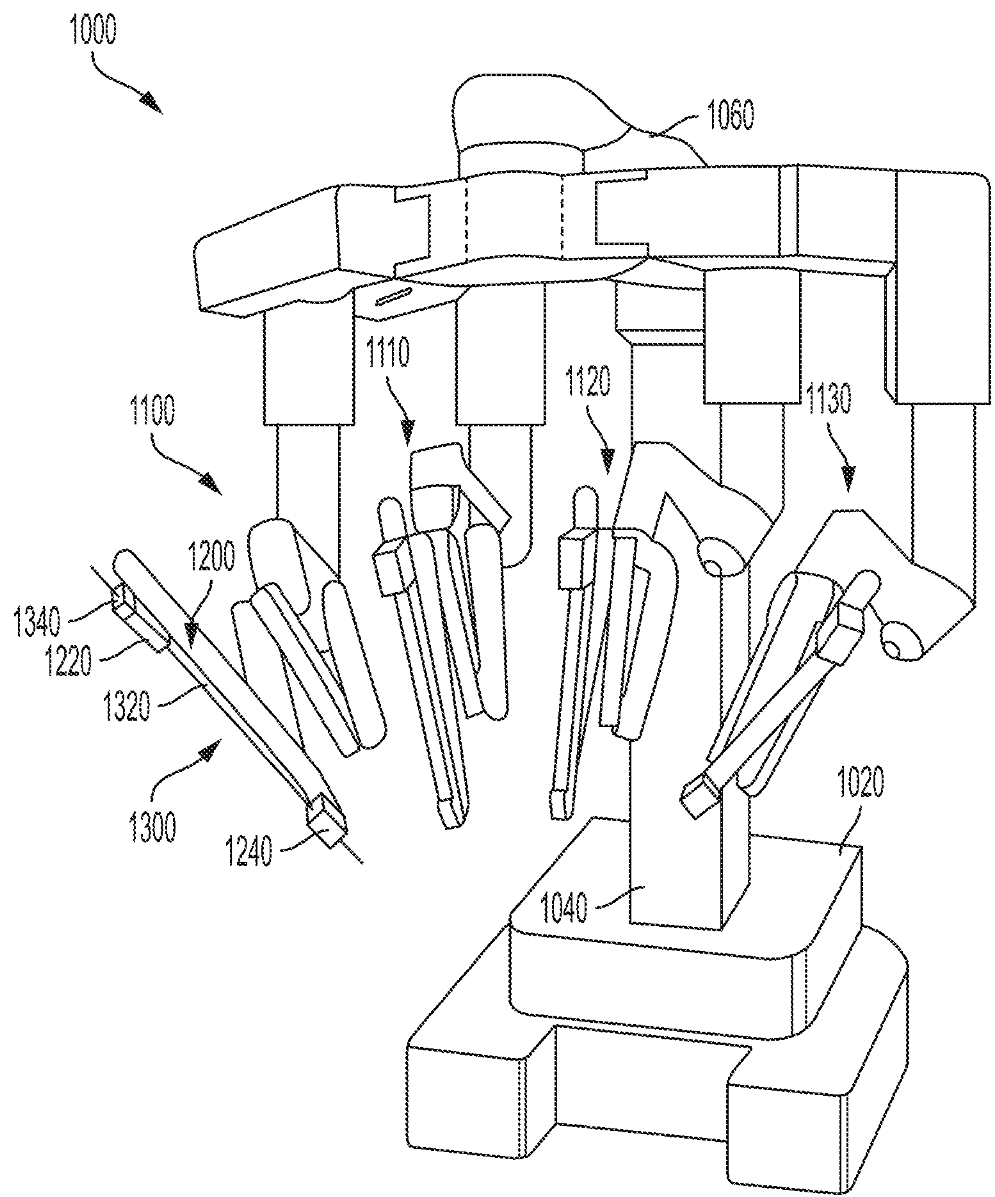
FIG. 25 is a perspective view of a manipulating system according to the present disclosure.

As shown in the embodiment of FIG. 25, manipulating system 1000 includes a base 1020, a main column 1040, and a main boom 1060 connected to main column 1040. Manipulating system 1000 also includes a plurality of arms 1100, 1110, 1120, 1130, which are each connected to main boom 1060. Arms 1100, 1110, 1120, 1130 each include an instrument mount portion 1200 to which an instrument 1300 may be mounted, which is illustrated as being attached to arm 1100. Portions of arms 1100, 1110, 1120, 1130 may be manipulated during a procedure according to commands provided by a user at a surgeon console (not shown). In an embodiment, signal(s) or input(s) transmitted from a surgeon console are transmitted to a controller, such as an auxiliary system, which may interpret the input(s) and generate command(s) or output(s) to be transmitted to the manipulating system 1000 to cause manipulation of an instrument 1300 (only one such instrument being mounted in FIG. 25) and/or portions of arm 1100 to which the instrument 1300 is coupled at the manipulating system 1000. One example of such an auxiliary system is the electronics cart described in U.S. Pat. Nos. 9,358,074 and 9,295,524, incorporated above, which may include, for example, one or both of control and imaging functionality. Instrument mount portion 1200 comprises a drive assembly 1220 and a cannula mount 1240, with a force transmission mechanism 1340 of the instrument 1300 connecting with the drive assembly 1220, according to an embodiment. Cannula mount 1240 is configured to hold a cannula 1360 through which a shaft 1320 of instrument 1300 may extend to a remote site during a procedure accessing the remote site. Drive assembly 1220 contains a variety of drive and other mechanisms that are controlled to respond to input commands at the surgeon console and transmit forces to the force transmission mechanism 1340 to actuate the instrument 1300, including for example, one or more of an end effector, joints, etc. of the instrument, as those skilled in the art are familiar with.

Although the embodiment of FIG. 25 shows an instrument 1300 attached to only arm 1100 for ease of viewing, an instrument may be attached to any and each of arms 1100, 1110, 1120, 1130. An instrument 1300 may be a surgical instrument with an end effector and/or one or more joints as discussed herein. A surgical instrument with an end effector may be attached to and used with any of arms 1100, 1110, 1120, 1130. However, the embodiments described herein are not limited to the embodiment of FIG. 25 and various other teleoperated, computer-assisted surgical system configurations may be used with the embodiments described herein. In some embodiments, the instrument 1300 can be or include an imaging device, such as an endoscopic or camera.

Although various embodiments described herein are discussed with regard to surgical instruments used with a manipulating system of a teleoperated surgical system, the present disclosure is not limited to use with surgical instruments for a teleoperated surgical system. For example, various embodiments of actuation members described herein can optionally be used in conjunction with hand-held, manually inserted laparoscopic instruments. Persons having ordinary skill in the art will appreciate that the present disclosure can be applied to a variety of surgical systems including automated or manual (hand-held) laparoscopic surgical systems, or with other surgical applications.

Various embodiments of the present disclosure provide an anchored guide device that facilitates positioning and stabilizing a cannula within a body wall. For example, various embodiments provide a relatively small diameter, single-walled guide tube that is part of a balloon trocar assembly. Anchored guide devices according to embodiments of the present disclosure may effectively interface with other components of a surgical system, such as facilitating conductive contact between a body wall and a conductive cannula or other instrument inserted through the anchored guide device, maintenance of insufflation pressure within a remote site of the body, and other functions necessary during a procedure being performed at a remote site.

This description and the accompanying drawings that illustrate embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term “about,” to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms “a,” “an,” and “the,” and any singular use of any word, include plural referents unless expressly and unequivocally limited to one referent. As used herein, the term “include” and its grammatical variants are intended to be non-limiting, such that recitation of items in a list is not to the exclusion of other like items that can be substituted or added to the listed items.

Further, this description’s terminology is not intended to limit the invention. For example, spatially relative terms—such as “beneath”, “below”, “lower”, “above”, “upper”, “proximal”, “distal”, and the like—may be used to describe one element’s or feature’s relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as “below” or “beneath” other elements or features would then be “above” or “over” the other elements or features. Thus, the exemplary term “below” can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A medical device, comprising:

a tube, comprising:

a proximal end, a distal end, a lateral wall extending from the proximal end to the distal end of the tube, the lateral wall having an inside surface surrounding a hollow interior of the tube, an engagement feature on the lateral wall, and a port proximate the proximal end;

an inflatable member located at a distal end portion of the tube;

a fluid passage fluidically coupling the port and the inflatable member, wherein the fluid passage extends longitudinally within a recessed channel formed in and extending longitudinally along the inside surface of the lateral wall, wherein the recessed channel is open along a side of the channel facing the hollow interior; and a repositionable anchor located on the tube proximal to the inflatable member and configured to selectively engage the engagement feature;

wherein in a first configuration of the medical device the repositionable anchor is translatable along the tube, and in a second configuration of the medical device the repositionable anchor is fixed in translation relative to the tube; and wherein the recessed channel is a first recessed channel and the medical device further comprises a second recessed channel formed in and extending longitudinally along the inside surface, wherein the first recessed channel is within the second recessed channel.

2. The medical device of claim 1, wherein:

the engagement feature on the lateral wall of the tube comprises a plurality of ratchet teeth; and the repositionable anchor comprises one or more ratchet pawls configured to engage the plurality of ratchet teeth.

3. The medical device of claim 2, wherein:

in the first configuration of the medical device, the one or more ratchet pawls are engaged with at least one of the plurality of ratchet teeth; and in the second configuration of the medical device, the one or more ratchet pawls are disengaged from the plurality of ratchet teeth.

4. The medical device of claim 3, wherein:

the repositionable anchor comprises one or more release portions and one or more resilient portions;

the one or more release portions are coupled to the one or more ratchet pawls by the one or more resilient portions; and in response to a force applied to the one or more release portions, the one or more resilient portions are deformable to move the one or more ratchet pawls from the first configuration to the second configuration of the medical device.

5. The medical device of claim 4, wherein the repositionable anchor comprises two release portions positioned diametrically opposite one another across the tube.

6. The medical device of claim 4, wherein the one or more release portions are configured to be manipulated by a user of the device to move the one or more ratchet pawls from the first configuration to the second configuration.

7. The medical device of claim 3, wherein:

in the first configuration of the medical device, the repositionable anchor is free to translate in a distal direction and a proximal direction along the tube; and in the second configuration of the medical device, the repositionable anchor is free to translate in the distal direction and prevented from translating in the proximal direction by engagement between the engagement feature on the lateral wall of the tube and the repositionable anchor.

8. The medical device of claim 1, wherein:

the engagement feature on the lateral wall of the tube comprise external tapered teeth extending around a portion of the tube in a circumferential direction;

the repositionable anchor further comprises:

an internal bore; and internal tapered teeth on a sidewall of the bore.

9. The medical device of claim 8, wherein:

in the first configuration of the medical device, the internal tapered teeth are disengaged from the external tapered teeth; and in the second configuration of the medical device, the internal tapered teeth are engaged with the external tapered teeth.

10. The medical device of claim 9, wherein the repositionable anchor is transitionable from the first to the second configuration of the medical device by rotating the repositionable anchor.

11. The medical device of claim 1, wherein the repositionable anchor comprises:

a first collar; and a second collar rotatably coupled to the first collar.

12. The medical device of claim 11, wherein:

the first collar comprises a first bore through which the tube passes;

the second collar comprises a second bore through which the tube passes; and the second bore comprises a longitudinal centerline offset from a center of rotation of the second collar.

13. The medical device of claim 12, wherein:

in the first configuration of the medical device, the longitudinal centerline of the second bore is coaxial with a longitudinal centerline of the tube; and in the second configuration of the medical device, the longitudinal centerline of the second bore is offset from the longitudinal centerline of the tube.

14. The medical device of claim 13, wherein in the second configuration of the medical device, mechanical interference between the first collar, the second collar, and the tube prevents the repositionable anchor from translating relative to the tube.

15. The medical device of claim 12, wherein:

the engagement feature of the tube comprise ribs extending longitudinally along a length of the tube;

the first collar comprises notches within the first bore configured to receive the longitudinal ribs; and engagement between the notches and longitudinal ribs prevent the first collar from rotating relative to the tube.

16. The medical device of claim 1, further comprising a cover covering the side of the recessed channel open to the hollow interior.

17. The medical device of claim 16, wherein the fluid passage is defined by the cover and the inside surface of the lateral wall in which the recessed channel is formed.

18. The medical device of claim 1, wherein a depth of the first recessed channel and the second recessed channel is defined along a radial dimension of the tube, and wherein the depth of the first recessed channel is larger than a depth of the second recessed channel.

19. The medical device of claim 18, further comprising a cover attached to the lateral wall of the tube, wherein the cover spans the second recessed channel and covers the first recessed channel.

20. The medical device of claim 1, further comprising the conduit member fit within the recessed channel, wherein the conduit defines the fluid passage.

* * * * *